United States Patent
Kapadia et al.

(10) Patent No.: US 11,961,615 B2
(45) Date of Patent: Apr. 16, 2024

(54) PATIENT SUPPORT APPARATUSES WITH DATA RETENTION MANAGEMENT

(71) Applicant: Stryker Corporation, Kalamazoo, MI (US)

(72) Inventors: Bhavin Kapadia, Portage, MI (US); Michael K. Holloway, Willshire, OH (US); Mark R. Bryant, LaOtto, IN (US)

(73) Assignee: Stryker Corporation, Kalamazoo, MI (US)

( * ) Notice: Subject to any disclaimer, the term of this patent is extended or adjusted under 35 U.S.C. 154(b) by 667 days.

(21) Appl. No.: 17/125,103

(22) Filed: Dec. 17, 2020

(65) Prior Publication Data

US 2021/0193312 A1 Jun. 24, 2021

Related U.S. Application Data

(60) Provisional application No. 62/951,404, filed on Dec. 20, 2019.

(51) Int. Cl.
*G16H 40/40* (2018.01)
*G05B 19/042* (2006.01)
(Continued)

(52) U.S. Cl.
CPC ........... *G16H 40/40* (2018.01); *G05B 19/042* (2013.01); *G06F 11/1448* (2013.01);
(Continued)

(58) Field of Classification Search
CPC ...... G16H 40/40; G16H 40/67; G05B 19/042; G05B 2219/2608; G06F 11/1448; G06F 2201/84; G06F 11/1004; H04L 67/12
(Continued)

(56) References Cited

U.S. PATENT DOCUMENTS 9,966,997 B2 5/2018 Hayes et al.
2014/0080413 A1* 3/2014 Hayes .................. H04B 5/02
455/41.1

(Continued)

OTHER PUBLICATIONS

Wikipedia "computer network" page retrieved from https://en.wikipedia.org/wiki/Computer_network (Year: 2023).*

(Continued)

*Primary Examiner* — Yair Leibovich
(74) *Attorney, Agent, or Firm* — Warner Norcross + Judd LLP

(57) ABSTRACT

A patient support apparatus, such as a bed, cot, stretcher, recliner, etc. includes a support deck, one or more lifts, and a plurality of circuit boards. Each circuit board includes an associated controller and memory, as well as a set of data associated with that circuit board. One of the controllers, such as, but not limited to, a main controller is adapted to automatically store a backup copy of the set of data associated with the other circuit boards. This main controller is further adapted to automatically determine if any of the circuit boards, including itself, are replacements of a previously installed circuit board. If so, the main controller uses the backup copy of the corresponding set of data to supply the replacement circuit board with the data from its previous counterpart, thereby ensuring that the historical data from past circuit boards is automatically transferred forward to their replacements.

20 Claims, 14 Drawing Sheets

(51) Int. Cl.
  *G06F 11/14*      (2006.01)
  *G16H 40/67*      (2018.01)
  *H04L 67/12*      (2022.01)

(52) U.S. Cl.
  CPC ............ *G16H 40/67* (2018.01); *H04L 67/12* (2013.01); *G05B 2219/2608* (2013.01); *G06F 2201/84* (2013.01)

(58) Field of Classification Search
  USPC .......................................................... 714/2
  See application file for complete search history.

(56)                References Cited

U.S. PATENT DOCUMENTS

2018/0110445 A1\*  4/2018  Bhimavarapu .......... A61G 7/00
2020/0394334 A1\*  12/2020  Bulut ..................... G06N 5/048

OTHER PUBLICATIONS

Wikipedia "consensus" page, retrieved from https://en.wikipedia.org/wiki/Consensus_(computer_science) (Year: 2023).\*
Stryker Operations Manual, Power-PRO TL Cot, Dec. 2019.

\* cited by examiner

PATENT SUPPORT APPARATUSES WITH DATA RETENTION MANAGEMENT

CROSS-REFERENCE TO RELATED APPLICATIONS

This application claims priority to U.S. provisional patent application Ser. No. 62/951,404 filed Dec. 20, 2019, by inventors Bhavin Kapadia et al. and entitled PATIENT SUPPORT APPARATUSES WITH DATA RETENTION MANAGEMENT, the complete disclosure of which is incorporated herein by reference.

BACKGROUND

The present disclosure relates to medical devices, such as, but not limited to, patient support apparatuses (e.g. beds, cots, stretchers, recliners, chairs, and the like) that include multiple printed circuit boards.

Modern day medical devices often utilize multiple microcontrollers that are mounted on multiple printed circuit boards within the medical device. Over the course of the lifetime of these medical devices, one or more of these printed circuit boards are often replaced for maintenance and/or upgrade purposes. The replacement of such circuit boards often leads to the permanent loss of data previously stored on the replaced circuit board.

SUMMARY

In its various embodiments, the present disclosure provides a medical device having multiple circuit boards that can be replaced without losing any of the data stored in the non-volatile memory of the replaced circuit board. Further, this retention of data from the replaced circuit boards is carried out automatically such that the technician, or other service person, replacing the circuit board does not need to take any manual steps to ensure the data is retained. In other embodiments, the various embodiments of the present disclosure are able to automatically detect and replace data from one or more corrupted files, and/or from one or more corrupted file systems. The medical devices are therefore able to more accurately retain data. Still further, in some embodiments, the data from one or more of the various circuit boards is forwarded to one or more remote servers and because the one or more circuit boards retain an accurate set of data, both generated by themselves and that generated from a previously installed board, the remote servers are able to maintain an accurate set of data regarding that particular medical device.

According to one embodiment of the present disclosure, a patient support apparatus is provided that includes a frame, a patient support surface, a lift, a first circuit board, a second circuit board, and a third circuit board. The patient support surface is supported on the frame and is adapted to support a patient thereon. The lift is adapted to raise and lower the patient support surface. The first circuit board includes a first controller and a first memory, and the first controller is adapted to store a first set of data in the first memory. The second circuit board includes a second controller and a second memory, and the second controller is adapted to store a second set of data in the second memory. The third circuit board includes a third controller and a third memory, and the third controller is adapted to store a third set of data in the third memory. The first controller is adapted to send a backup copy of the first set of data to the third circuit board, and the second controller is adapted to send a backup copy of the second set of data to the third circuit board. The third controller is further adapted to store the backup copy of the first set of data and the backup copy of the second set of data in the third memory.

According to other embodiments of the present disclosure, the third controller is further adapted to send a first backup copy of the third set of data to the first circuit board and a second backup copy of the third set of data to the second circuit board. In such embodiments, the first controller is also adapted to store the first backup copy of the third set of data in the first memory and the second controller is also adapted to store the second backup copy of the third set of data in the second memory.

In some embodiments, the first set of data includes a first identifier for the first circuit board and the second set of data includes a second identifier for the second circuit board. The third set of data may also include a third identifier for the third circuit board. When included, the first controller may be adapted to store a first backup copy of the third identifier in the first memory and the second controller may be adapted to store a second backup copy of the third identifier in the second memory.

In some embodiments, the first controller, in response to a first triggering condition, is adapted to resend back to the third circuit board the first backup copy of the third identifier stored in the first memory. In such cases, the third controller is adapted to compare the resent first backup copy of the third identifier to the third identifier stored in the third memory.

In some embodiments, the second controller, in response to a second triggering condition, is adapted to resend back to the third circuit board the second backup copy of the third identifier stored in the second memory. In such embodiments, the third controller is adapted to compare the resent second backup copy of the third identifier to the third identifier stored in the third memory.

If neither the resent first backup copy of the third identifier nor the resent second backup copy of the third identifier match the third identifier stored in the third memory, in some embodiments, the third controller is further adapted to conclude that the third circuit board is a replacement of a previously installed third circuit board.

The third controller, in some embodiments, is further adapted, after determining that the third circuit board is a replacement of a previously installed circuit board, to replace the third identifier stored in the third memory with at least one of the resent first backup copy of the third identifier from the first memory or the resent second backup copy of the third identifier from the second memory.

In some embodiments, if the resent first backup copy of the third identifier matches the third identifier stored in the third memory but the resent second backup copy of the third identifier does not match the third identifier stored in the third memory, the third controller is further adapted to conclude that the second circuit board is a replacement of a previously installed second circuit board.

When the third controller determines that the second circuit board is a replacement circuit board, the third controller is adapted, in some embodiments, to resend back to the second circuit board the second set of data stored in the third memory, and the second controller is further adapted to replace the second set of data stored in the second memory with the resent second set of data received from the third controller.

In some embodiments, the third identifier is a checksum value of an identification file stored in the third memory, and the identification file contains at least one unique string of characters uniquely identifying the third circuit board.

The first circuit board, in some embodiments, is coupled to a motor adapted to drive the lift. In such embodiments, the first set of data may include usage data regarding the motor.

The first controller is adapted to detect if the first set of data stored in the first memory includes corrupt data, in some embodiments. If so, the first controller is further adapted to replace the corrupt data with at least a portion of the backup copy of the first set of data stored in the third memory and received back from the third circuit board.

In some embodiments, the patient support apparatus further includes a transceiver adapted to communicate with an off-board server. The transceiver is further adapted to transmit at least a portion of the resent second set of data received from the third controller to the off-board server after the second circuit board has been replaced.

According to another embodiment of the present disclosure, a patient support apparatus is provided that includes a frame, a patient support surface, a lift, a first circuit board, a second circuit board, and a third circuit board. The patient support surface is supported on the frame and is adapted to support a patient thereon. The lift is adapted to raise and lower the patient support surface. The first circuit board includes a first controller and a first memory, and the first controller is adapted to store a first set of data in the first memory. The second circuit board includes a second controller and a second memory, and the second controller is adapted to store a second set of data in the second memory. The third circuit board includes a third controller and a third memory, and the third controller is adapted to store a third set of data in the third memory. The third controller is also adapted to automatically store a backup copy of the first set of data in the third memory, to determine if the first circuit board is a replacement of a previously installed first circuit board, and if so, to forward the backup copy of the first set of data to the first circuit board.

In other aspects of the present disclosure, the first controller is further adapted to automatically store a backup copy of the third set of data in the first memory, and the third controller is further adapted to automatically determine if the third circuit board is a replacement of a previously installed third circuit board. If so, the third controller is adapted to retrieve a backup copy of the third set of data from the first memory and to replace the third set of data stored in the third memory with the backup copy of the third set of data from the first memory.

In some embodiments, in response to the third controller determining that the third circuit board is a replacement of a previously installed third circuit board, the third controller is further adapted to retrieve another backup copy of the first set of data from the first circuit board, to retrieve another backup copy of the second set of data from the second circuit board, and to store the another retrieved copies of the first and second sets of data in the third memory.

The third controller, in some embodiments, is adapted to automatically determine if the third circuit board is a replacement of a previously installed third circuit board by comparing an identifier associated with the third circuit board and stored in the third memory with a first backup identifier stored in the first memory and a second backup identifier stored in the second memory. In such embodiments, if the identifier is different from both the first backup identifier and the second backup identifier, the third controller determines that the third circuit board is a replacement of a previously installed third circuit board.

In some embodiments, the first controller is further adapted to determine if any of the first set of data stored in the first memory is corrupt and, if so, to retrieve from the third circuit board the backup copy of the first set of data stored in the third memory. The first controller is further adapted to overwrite the corrupt data with the retrieved backup copy of the first set of data.

The first set of data, in some embodiments, includes an identifier of the first circuit board. In such embodiments, the third controller is adapted to determine if the first circuit board is a replacement of a previously installed first circuit board by comparing the identifier of the first circuit board stored in the first memory with a backup copy of the identifier stored in the third memory.

In some embodiments, the patient support apparatus is a cot, while in other embodiments the patient support apparatus is a bed, a stretcher, a recliner, or other type of patient support apparatus. In still other embodiments, a thermal control unit includes multiple circuit boards of the type described herein and is adapted to perform one of more of the functions described herein such as, but not limited to, the automatic transfer of previously generated data from a first circuit board to a replacement for that circuit board.

Before the various embodiments disclosed herein are explained in detail, it is to be understood that the claims are not to be limited to the details of operation, to the details of construction, or to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 4 is a block diagram of the internal circuitry of the patient support apparatus of FIG. 1, as well as an example of the type of network infrastructure which the patient support apparatus is able to communicate with;

DETAILED DESCRIPTION OF THE EMBODIMENTS

Figure 1:
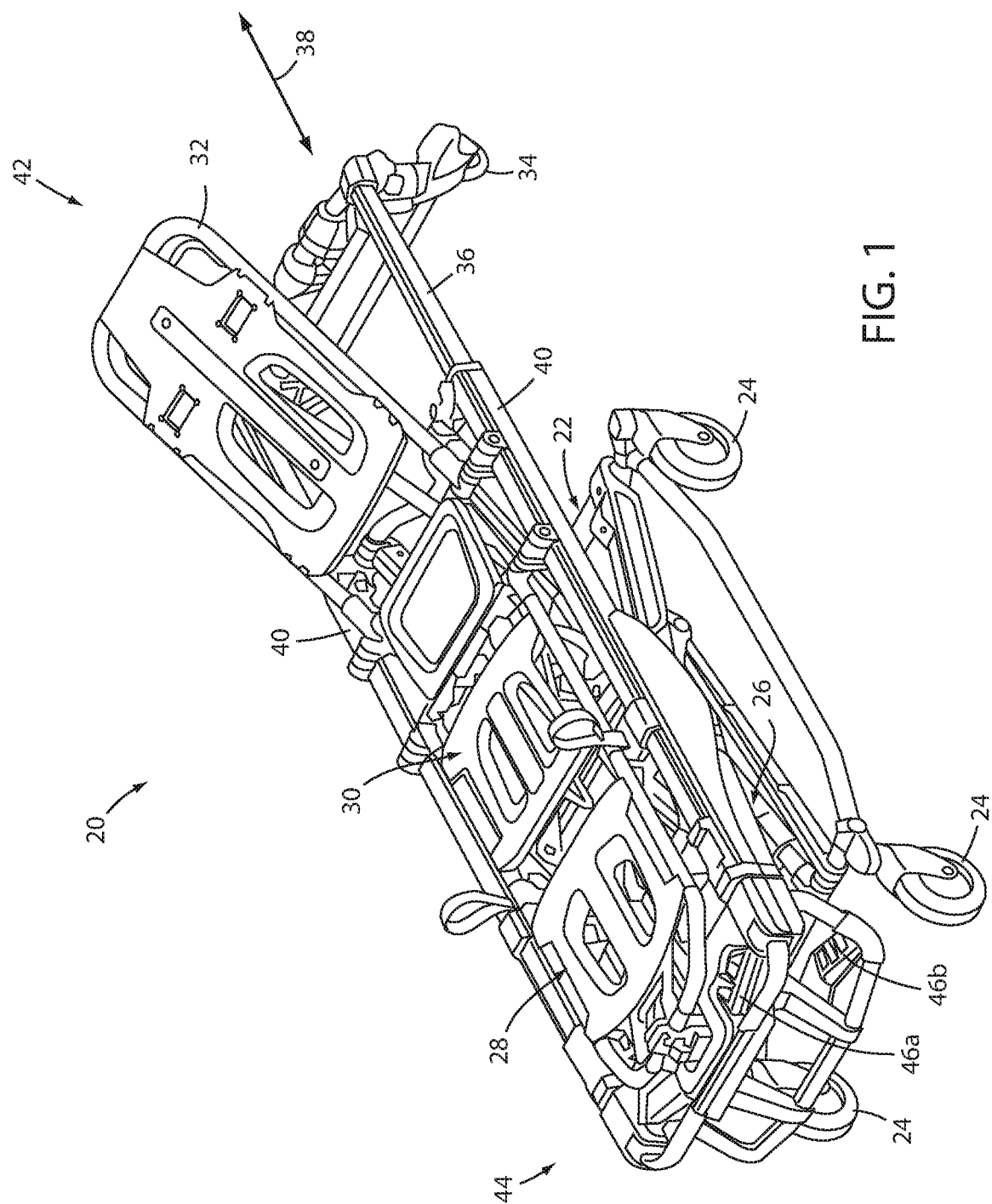
FIG. 1 is perspective view of a patient support apparatus into which one or more of the features of the present disclosure may be incorporated.

A patient support apparatus 20 according to one embodiment of the present disclosure is shown in FIG. 1. Although the particular form of patient support apparatus 20 illustrated in FIG. 1 is a cot adapted for use with an ambulance, in a hospital, or in some other type of setting, it will be understood that the patient support apparatus 20 could, in different embodiments, be a bed, a stretcher, a gurney, a recliner, or any other structure capable of supporting and/or transporting a patient.

In general, the patient support apparatus 20 includes a base 22 having a plurality of wheels 24, a lift subsystem 26 supported on the base, a litter frame 28 supported on the lift subsystem 26, and a support deck 30 supported on the litter frame 28. Lift subsystem 26 is adapted to raise and lower litter frame 28 with respect to base 22. Lift subsystem 26 may include one or more hydraulic actuators, electric actuators, or any other suitable devices for raising and lowering litter frame 28 with respect to base 22.

Litter frame 28 provides a structure for supporting support deck 30. Support deck 30 provides a cushioned support surface for a person to lie and/or sit thereon. The support deck 30 is made of a plurality of sections, some of which are pivotable about generally horizontal pivot axes. In the embodiment shown in FIG. 1, the support deck 30 includes a head section 32, which is also sometimes referred to as a Fowler section, and which is pivotable about a generally horizontal pivot axis between a generally horizontal orientation (not shown in FIG. 1) and a plurality of raised positions (one of which is shown in FIG. 1).

Patient support apparatus 20 also includes a pair of upper wheels 34 that are coupled to a telescoping arm 36. Telescoping arm 36 is movable back and forth in a direction indicated by arrow 38. This telescoping movement is accommodated by a pair of side arms 40 on litter frame 28 that have an internal diameter larger than the external diameter of telescoping arms 36 so as to receive the telescoping arms 36 therein. The telescoping movement of arms 36 helps facilitate the ingress and egress of patient support apparatus 20 into and out of emergency vehicles, such as ambulances, rescue squads, helicopters, or the like. More specifically, by setting upper wheels 34 on top of a floor inside the ambulance, or other vehicle, a head end 42 of patient support apparatus 20 can be supported via upper wheels 34, thereby enabling a caregiver at a foot end 44 of patient support apparatus 20 to raise or lower base 22 while manually lifting the foot end 44 of patient support apparatus 20.

Figure 2:
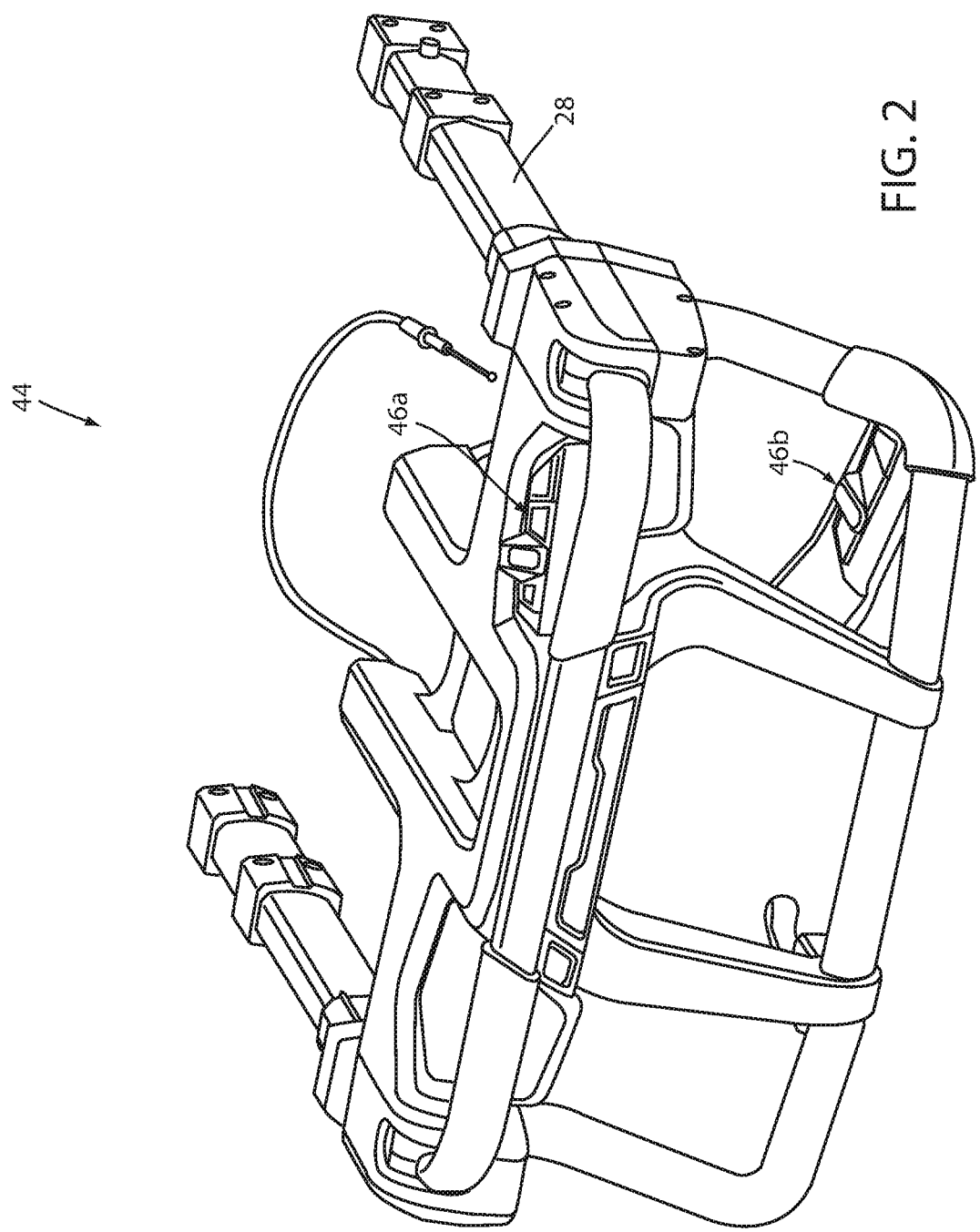
FIG. 2 is a close-up perspective view of the foot end of the patient support apparatus of FIG. 1.
Figure 3:
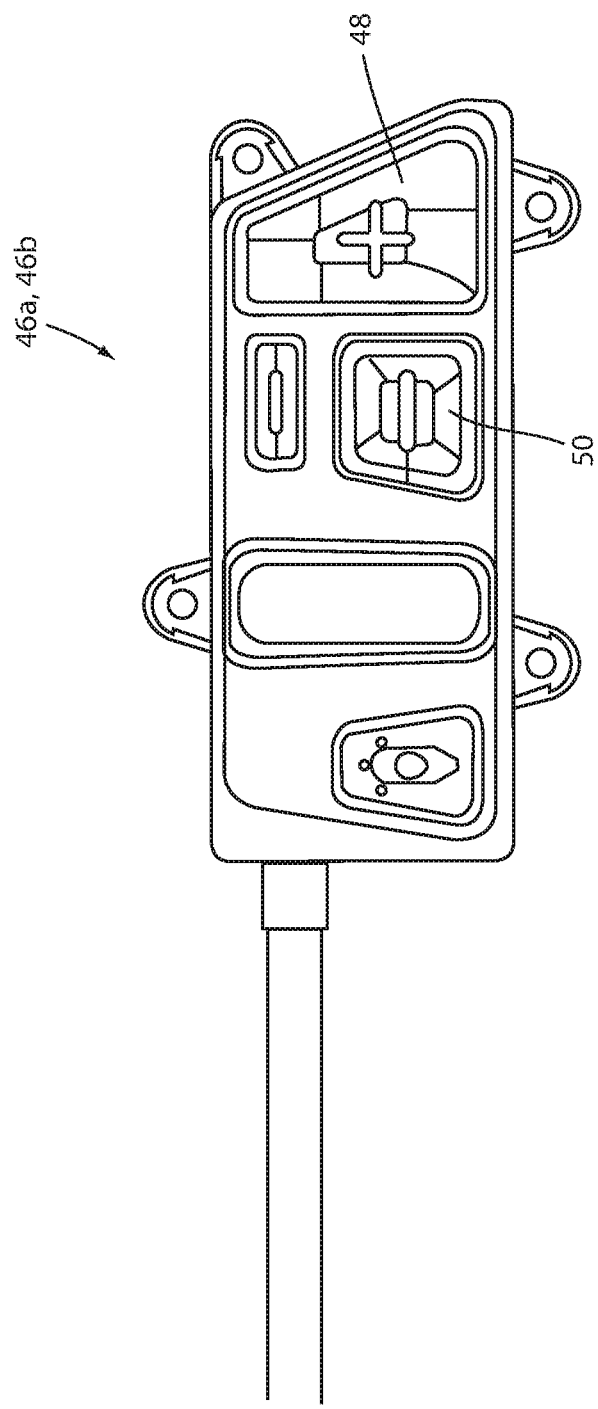
FIG. 3 is a plan view of one of the foot end user interfaces of the patient support apparatus of FIG. 1.

Patient support apparatus 20 further includes one or more user interfaces or control panels 46 that enable a user of patient support apparatus 20, such as a patient and/or an associated caregiver, to control one or more aspects of patient support apparatus 20. In the embodiment shown in FIG. 1, patient support apparatus 20 includes an upper footboard control panel 48a and a lower footboard control panel 48b. Both of these control panels 46a and 46b include the same controls, which are shown in more detail in FIG. 2.

Controls panels 46a and 46b each include a raise control 48 and a lower control 50. Raise control 48, when pressed, increases the vertical distance between base 22 and litter frame 28. When patient support apparatus 20 is supported on the ground, the result of pressing raise control 48 is to raise the height of litter frame 28 with respect to the ground. When the litter frame 28 of patient support apparatus 20 is supported on a vehicle-installed cot-lifting system, such as, but not limited to, the Stryker Power-LOAD® cot fastener system, pressing raise control 48 causes base 22 to lift upwardly into closer proximity to litter frame 28. Lower control 50 does the opposite of raise control 48. That is, when patient support apparatus 20 is supported on the ground, the result of pressing lower control 50 is to lower the height of litter frame 28 with respect to the ground; and when litter frame 28 is supported on an ambulance lifting system, pressing lower control 50 causes base 22 to drop downwardly and move away from litter frame 28. Raise and lower controls 48 and 50 therefore interact with and control the movement of lift subsystem 26.

In some embodiments, patient support apparatus 20 may include additional controls on one or more of control panels 48a and/or 48b. Such controls may include a control for communicating with and/or controlling one or more aspects of a cot lifting system, such as controls to translate patient support apparatus 20 into and/or out of the vehicle in which the cot-lifting system is mounted. As noted, one type of cot-lifting system to which patient support apparatus 20 may be adapted to both physically couple to and electrically communicate with is the Power-LOAD® cot fastener system manufactured and sold by Stryker Corporation of Kalamazoo, Michigan. Further details of this cot fastener system are described in the Operations Manual for the Power-LOAD® cot fastener system, which was published in June 2019 by Stryker Corporation and assigned document identifier 6390-609-001 Rev. B.1, the complete disclosure of which is incorporated herein by reference. Still other types of cot fastening systems may be utilized, and patient support apparatus 20 may include one or more controls for these other cot fastening systems, and/or still other type of controls.

The detailed mechanical construction of patient support apparatus 20 may take on any of a variety of different forms. In one embodiment, the mechanical construction is the same as that described in commonly assigned, U.S. Pat. No. 7,725,968 issued to Clifford Lambarth and entitled AMBULANCE COT WITH RETRACTABLE HEAD SECTION AND CONTROL SYSTEM THEREFOR, the complete disclosure of which is hereby incorporated herein by reference. In other embodiments, the mechanical construction of patient support apparatus 20 may be the same as the Power-PRO™ TL Cot manufactured by Stryker Corporation of Kalamazoo, Michigan, as described in the Maintenance Manual for the Power-PRO™ TL Cot, which was published in July 2019 by Stryker Corporation and assigned document number 6550-109-002 Rev. D.0, the complete disclosure of which is incorporated herein by reference. Still other types of mechanical constructions of patient support apparatus 20 may also be utilized.

Figure 4:
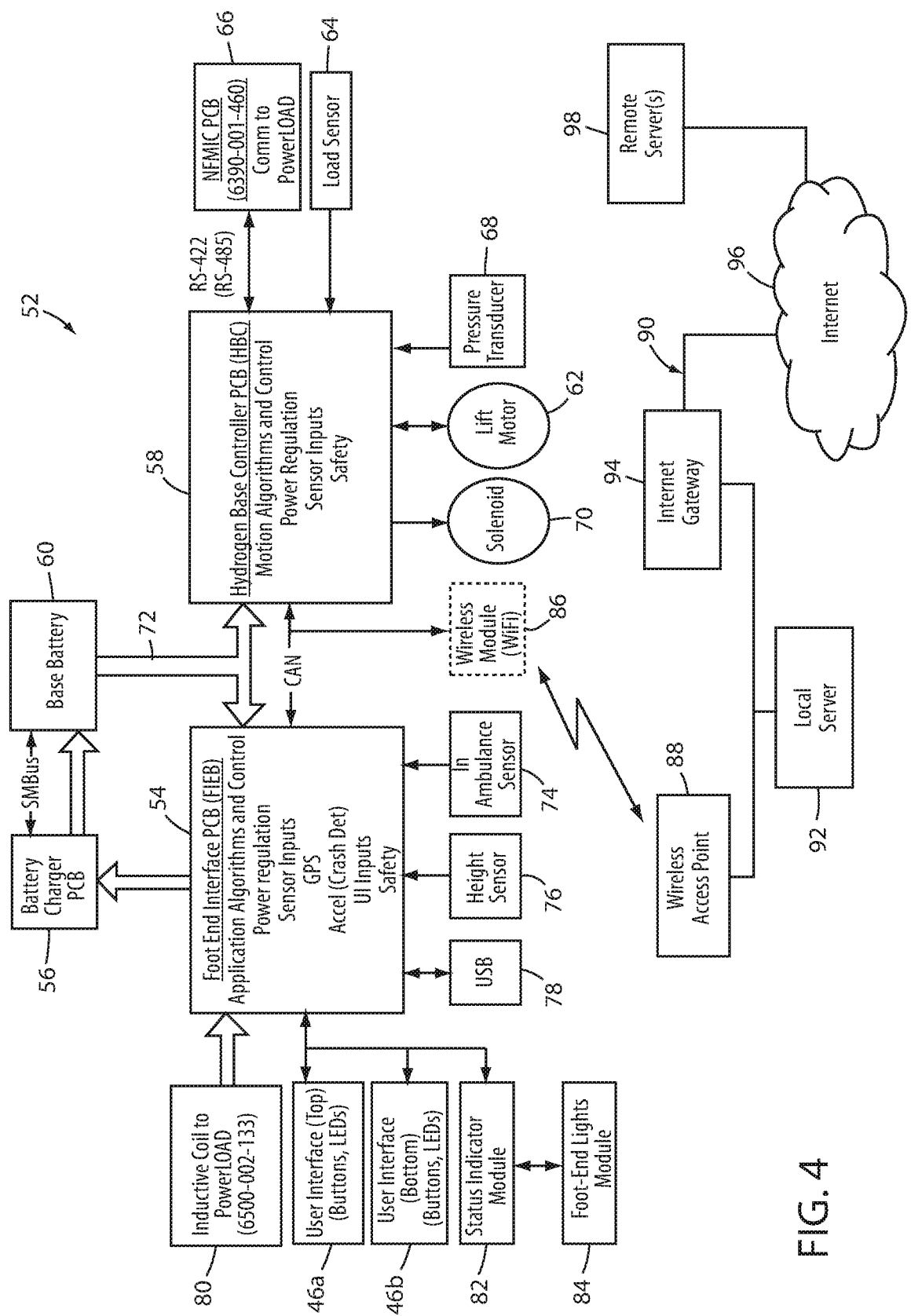

FIG. 4 illustrates one suitable embodiment of a control system 52 for patient support apparatus 20. Control system 52 includes a main circuit board 54, a battery charger circuit board 56, and an actuator control circuit board 58. Each of the circuit boards 54, 56, and 58 may be conventional printed circuit boards having a plurality of electronics mounted thereto by any suitable method, such as, but not limited to, through-hole technology, surface-mount technology, or other methods. The function and contents of circuit board 54, 56, and 58 are described in greater detail below.

In addition to circuit boards 54, 56, and 58, control system 52 includes a battery 60, upper and lower control panels 46a and 46b, a lift motor 62, a load sensor 64, a communication interface 66 for a cot fastening system, a pressure transducer 68, a solenoid 70, a communication bus 72, an in-ambulance sensor 74, a height sensor 76, a Universal Serial Bus (USB) port 78, an inductive power coil 80, a status indicator module 82, and a foot end light module 84. Main circuit board 54 is in direct communication with in-ambulance sensor 74, height sensor 76, USB port 78, controls panels 48a, 48b, inductive power coil 80, status indicator module 82, and foot end lights module 84. Battery charger circuit board 56 is in direct communication with, and charges, battery 60. Actuator control circuit board 58 is in direct communication with lift motor 62, load sensor 64, communication interface 66, pressure transducer 68, and solenoid 70. Each of the three circuit boards 54, 56, and 58 are in communication with each other over communication bus 72 which, in some embodiments, is a Controller Area Network (CAN) bus. It will be understood by those skilled in the art, however, that other types of communication buses, and/or other types of communication structures and/or protocols, may be used for communication between circuit boards 54, 56, and 58.

Main circuit board 54 is configured to regulate the power delivered by battery 60 to all of the components of patient support apparatus 20. Main circuit board 54 is also configured to receive various sensor inputs, such as those from in-ambulance sensor 74 and height sensor 76; to interact with a diagnostic tool and/or other external device that is adapted to communicate with main circuit board 54 via USB port 78; to control the inductive receipt of electrical power from electrical coil 80; to carry out the commands received from control panels 46a, b; and to oversee the operation of status indicator module 82 and foot end lights module 84.

In-ambulance sensor 74 (FIG. 4) detects when patient support apparatus 20 is positioned inside of an ambulance. Height sensor 76 is adapted to detect a height of litter frame 28 with respect to base 22 and may be any suitable sensor. USB port 78 is a conventional USB port adapted to allow an external device to communicate with patient support apparatus 20, such as for diagnostic purposes, software updates, servicing, etc. Inductive coil 80 is adapted to allow patient support apparatus 20 to inductively receive electrical power that may be used to power the functions of patient support apparatus 20 and/or to recharge battery 60. Such inductive recharging typically takes place while patient support apparatus 20 is positioned within an ambulance or other vehicle which has a complementary inductive coil positioned in a location suitably adjacent to coil 80 to allow inductive energy transfer therebetween. In some embodiments, inductive coil 80 and patient support apparatus 20 may be configured in any of the manners disclosed in commonly assigned U.S. Pat. No. 9,289,336 issued to Lambarth et al. and entitled PATIENT SUPPORT WITH ENERGY TRANSFER, the complete disclosure of which is incorporated herein by reference. Inductive coil 80 may also and/or alternatively be used for wireless communication, such as for any of the wireless communication configurations disclosed in commonly assigned U.S. Pat. No. 9,966,997 issued to Hayes et al. and entitled COMMUNICATION SYSTEMS FOR PATIENT SUPPORT APPARATUSES, the complete disclosure of which is also incorporated herein by reference.

Status indicator module 82 (FIG. 4) provides an indication of the status of patient support apparatus 20, such as, but not limited to, the charge state of battery 60. Foot end lights module 84 includes a plurality of lights that are controller by status indicator module 82, and the selective illumination and non-illumination of these lights provides information to the user of patient support apparatus 20, such as the charge status of battery 60.

Battery charger circuit board 56 controls the charging of battery 60, which is a rechargeable battery of any suitable type, such as, but not limited to, a nickel-cadmium battery, a lithium-ion battery, or another type of battery. Battery charger circuit board 56 communicates with main circuit board 54 and actuator control circuit board 58 over the communication bus 72.

Actuator control circuit board 58 (FIG. 4) controls the actuator(s) that power the lift subsystem 26. In some embodiments, a single motorized actuator is used to drive lift subsystem 26, while in other embodiments, multiple actuators are used to drive lift subsystem 26. In the illustrated embodiment, a single actuator is used that includes lift motor 62. Actuator control circuit board 58 controls the operation of lift motor 62, thereby controlling the variable distance between base 22 and litter frame 28. Solenoid 70 is also in communication with, and controlled by, actuator control circuit board 58. Pressure transducer 68 is adapted to detect when wheels 24 are supporting patient support apparatus 20 on the ground (as opposed to patient support apparatus 20 being supported by a cot fastening system). Pressure transducer 68 detects pressure generated when wheels 24 are supporting patient support apparatus 20 and reports this to actuator control circuit board 58. In some embodiments, actuator control circuit board 58 changes the speed at which lift subsystem 26 retracts and extends based upon the outputs of pressure transducer 68. In some embodiments, lift subsystem 26 is constructed in any of the manners, and/or has its speed controlled in any of the manners, disclosed in commonly assigned U.S. patent application Ser. No. 62/926,711 filed Oct. 28, 2019, by inventors Chad Souke et al. and entitled HYDRAULIC VALVE AND SYSTEM, the complete disclosure of which is incorporated herein by reference. In other embodiments, lift subsystem 26 may be constructed in the same manner as, and/or operated in the same manner as, the lift system disclosed in commonly assigned U.S. patent application Ser. No. 62/926,712 filed Oct. 28, 2019, by inventors Ross Lucas et al. and entitled HYDRAULIC CIRCUIT FOR A PATIENT HANDLING APPARATUS, the complete disclosure of which is also incorporated herein by reference. Still other constructions and/or functional control aspects of lift subsystem 26 may be utilized.

Communication interface 66 (FIG. 4) is adapted to communicate with a cot fastening system mounted in the interior of a vehicle adapted to transport patient support apparatus 20, such as, but not limited to, an ambulance. A variety of different types of cot fastening systems may be used with patient support apparatus 20 including, but not limited to, the PowerLOAD® cot fastening system mentioned above. In some embodiments, patient support apparatus 20 is constructed without the ability to be handled by a cot fastening system, and/or it is constructed without the ability to electronically communicate with a cot fastening system. In such cases, communication interface 66 may be omitted. When included, communication interface 66 allows the user of patient support apparatus 20 to utilize control panels 46a, 46b to control one or more aspects of the cot fastening system, such as, but not limited to, the extension and retraction of the patient support apparatus 20 out of and into the ambulance, or other emergency vehicle. Communication interface 66 accomplishes this by forwarding the commands received at control panels 46a and/or 46b to the cot fastening system. In some embodiments, the commands are forwarded via inductive communication, while in other embodiments, other types of wired or wireless communication may take place between patient support apparatus 20 and the cot fastening system.

Load sensor 64 (FIG. 4) is adapted to detect how much of a load the patient support apparatus 20 is carrying (e.g. patient weight plus any accessories supported on patient support apparatus 20). Load sensor 64 may be any suitable sensor, or set of sensors, that are able to detect how much weight is being supported on patient support apparatus 20. Actuator control circuit board 58 may utilize this weight information when controlling the lift subsystem 26 (e.g. it may change the speed of operation of lift subsystem 26), and/or actuator control circuit board 58 may forward this weight information to a cot fastening system via communication interface 66.

In some embodiments, patient support apparatus 20 includes an additional circuit board, such as a wireless communication circuit board 86. In the illustrated embodiment (FIG. 4), wireless communication circuit board 86 is a circuit board that includes a WiFi transceiver (IEEE 802.11 . . . ) that is adapted to communicate with one or more wireless access points 88 of one or more local area networks 90 when patient support apparatus 20 is within communication range of the local area network 90. The local area network may vary depending upon which medical facility patient support apparatus 20 is brought to. The computers coupled to that local area network 90 may also vary. In the illustrative embodiment of FIG. 4, network 90 is shown to include at least one local server 92, and an Internet gateway 94 that couples network 90 to the Internet 96. Still further, in some embodiments, patient support apparatus 20 is configured to utilize to the network 90 to communicate with one or more remote servers 98 that are coupled to network 90 via Internet 96 and Internet gateway 94. In some embodiments, patient support apparatus 20 is configured to communicate with one or more remote servers 98 that are part of an equipment management system. In at least one of these embodiments, the equipment management system and/or wireless communication circuit board 86 are constructed in any of the various manners disclosed in commonly assigned PCT patent application PCT/US2017/041681 filed Jul. 12, 2017, by inventors David Becker et al. and entitled EQUIPMENT MANAGEMENT SYSTEM, the complete disclosure of which is incorporated herein by reference.

In some embodiments, the vehicle in which patient support apparatus 20 is transported may have a WiFi access point that allows patient support apparatus 20 to communicate wirelessly with the vehicle's network and any of the servers, or other computer devices, that are communicatively coupled to the vehicle's network. In still other embodiments, wireless communication module 86 may be configured to communicate using other communication protocols, such as, but not limited to, Bluetooth, ZigBee, and/or others. In still other embodiments, wireless communication circuit board 86 may be omitted entirely. When included, however, wireless communication circuit board 86 communicates with the other circuit boards 54, 56, and 58 via communication bus 72.

It will of course be understood that control system 52 (FIG. 4) of patient support apparatus 20 may be varied in a wide variety of manners from what is shown in FIG. 4 and from what has been described herein. Such modifications include, but are not limited to, the omission of one or more of the components that are in direct communication with any of the circuit boards 54, 56, 58 and/or 86, as well as the addition of one or more additional circuit boards and/or the removal of one or more of the illustrated circuit boards 54, 56, 58, and/or 86.

Figure 5:
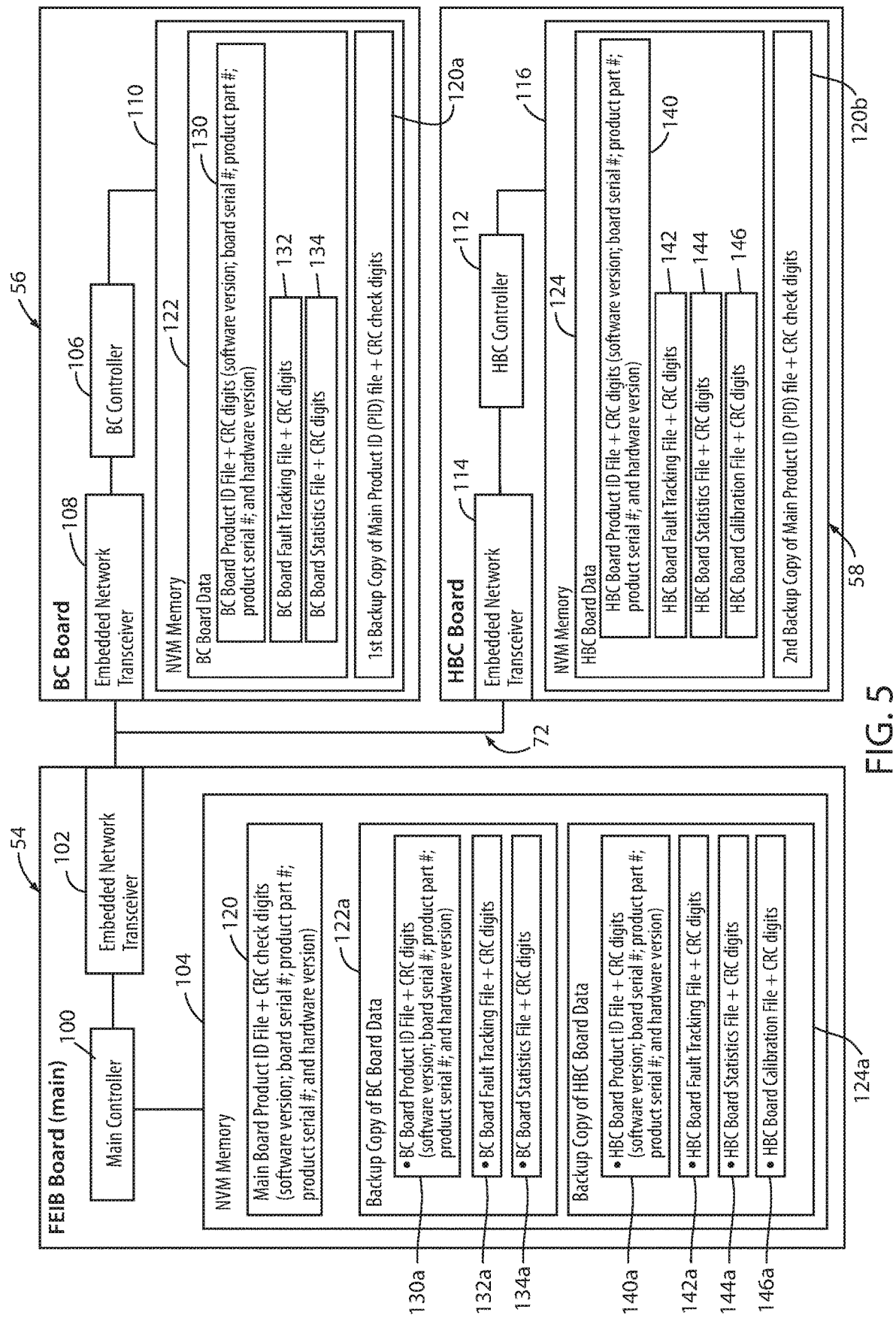
FIG. 5 is a block diagram of the basic components of the circuit boards of the patient support apparatus of FIG. 1, including a portion of the contents of the non-volatile memory of these circuit boards.

FIG. 5 illustrates in greater detail several of the components of each of the circuit boards 54, 56, and 58, including a portion of the contents of the non-volatile memory contained within each of these boards. As shown therein, main circuit board 54 includes a main controller 100, a main communication bus transceiver 102, and a main memory 104. Similarly, battery charger circuit board 56 includes a battery charging controller 106, a battery charging network transceiver 108, and a battery charging memory 110; and actuator control circuit board 58 includes an actuator controller 112, an actuator transceiver 114, and an actuator memory 116.

In the illustrated embodiment, each of controllers 100, 106, and 112 is a conventional microcontroller. In general, each of the circuit boards 54, 56, and 58 include, in addition to the microcontrollers discussed herein, additional circuitry and programming for carrying out the functions described herein, as would be known to one of ordinary skill in the art. Such additional circuitry may include, but is not limited to, field programmable gate arrays, volatile memory, discrete circuitry, and/or other hardware, software, or firmware that is capable of carrying out the functions described herein. The instructions followed by each of the microcontrollers in carrying out the functions described herein, as well as the data necessary for carrying out these functions, are stored in memories (such as, but not necessarily, memories 104, 110, and 116) mounted to each of the circuit boards, or otherwise accessible to each microcontroller.

As was noted, circuit boards 54, 56, and 58 communicate with each other over communication bus 72, which may be a Controller Area Network (CAN) bus that operates in accordance with one or more of the ISO standards 11898-1, 11898-2, and/or 11898-3. Alternatively, or additionally, two or more of the circuit boards of control system 52 may communicate using the CAN FD 1.0 (Flexible Data-Rate) standard. Still further, some of the circuit boards of control system 52 may alternatively or additionally communicate using the Local Interconnect Network (LIN) serial network protocol. Indeed, in some embodiments, two or more of the circuit boards of control system 52 may translate messages from one protocol to another, such as is disclosed in commonly assigned U.S. patent application Ser. No. 15/903,477 filed Feb. 23, 2018, by inventors Krishna Bhimavarapu et al. and entitled PATIENT CARE DEVICES WITH ON-BOARD NETWORK COMMUNICATION, the complete disclosure of which is hereby incorporated herein by reference.

Memories 104, 110, and 116 are non-volatile memories that are adapted to retain their data contents after electrical power is terminated. It will be understood by those skilled in the art that, although not shown in FIG. 5, each controller 100, 106, and 112 includes one or more sets of Random Access Memory (RAM) that may be volatile memory that loses its data when electrical power is terminated. In at least one embodiment, memories 110 and 116 are conventional flash memory while memory 104 is a magnetic memory (e.g. a conventional hard drive, or the like). In other embodiments, other types of memory may be used and/or all of the memories 104, 110, and 116 may be of the same type, or they may all be of different type. As with main controller 100 and main transceiver 102, main memory 104 is physically located on main circuit board 54. Similarly, battery charger controller 106, battery charger transceiver 108, and battery charger memory 110 are physically located on battery charger circuit board 56; and actuator controller 112, actuator transceiver 114, and actuator memory 116 are physically located on actuator control circuit board 58.

Main controller 100 is adapted to store at least three data sets in its memory 104. In the illustrated embodiment (FIG. 5), these three data sets include a main circuit board product ID data set 120, a backup copy 122a of battery charger circuit board data 122, and a backup copy 124a of actuator control circuit board data 124. Main product ID data set 120 contains data that is specific to main circuit board 54, including such data that distinguishes main circuit board 54 from replacements of main circuit board 54. In the illustrated embodiment, main control product ID data set 120 includes five identifiers: (1) a software identifier indicating what version of software is installed on main circuit board 54; (2) a circuit board serial number that uniquely identifies main circuit board 54; (3) a product part number that identifies what part of patient support apparatus 20 main circuit board 54 is; (4) a product serial number that uniquely identifies the particular patient support apparatus 20 into which main circuit board 54 is integrated; and (5) a hardware version that identifies the particular hardware version that is currently installed on main circuit board 54. It will be understood that the precise contents of the main circuit board product ID data set 120 may be varied, including further additions to the aforementioned data, omissions of one or more of these data items, and/or a combination of both additions and omissions.

In some embodiments, main controller 100 stores these five data items—the software identifier, circuit board serial number, product part number, product serial number, and hardware version—in a file, and concurrently generates an error-detecting code for that file so that the contents of that file can be checked for accuracy. Although other types of error detecting codes may be used, in at least one embodiment, controller 100 is programmed to generate a 16 bit Cyclical Redundancy Check (CRC) that accompanies the file containing the five data items mentioned above. The sixteen bit CRC number is stored along with, and in some cases as part of, the main circuit board PID data set 120. Whenever the contents of any of the five data items mentioned above are changed, controller 100 generates a new CRC value for the updated data and stores it in memory 104.

Further, whenever the contents of file 120 are retrieved (e.g. read), controller 100 is programmed to examine the CRC value and the contents of file 120 read from memory 104 to determine if there is any error with the retrieved data. In other words, main controller 100 stores file 120 and the CRC value as a codeword and, upon subsequent reading of the codeword, it compares the CRC check value with one freshly calculated by main controller 100, or alternatively performs a CRC on the whole codeword and compares the resulting check value with an expected residue constant. If the CRC values do not match, or the residue constant does not match an expected residue constant, main controller 100 concludes that there is an error in the codeword, and thus the data stored within data set 120.

As will be discussed in greater detail below, control system 52 is configured, in at least some embodiments, to overcome an error detected via the CRC check value by retrieving the contents of data set 120 from one (or both) of the backup copies of this data stored on circuit boards 56 and 58. That is, main controller 100 is configured to periodically send a copy of a data set 120 to both battery charger circuit board 56 and circuit board 58, and these circuit boards in turn store these backup copies in their own respective memories. Thus, as can be seen in FIG. 5, battery charger circuit board 56 includes a first backup copy 120a of main circuit board's PID data set 120, and actuator control circuit board 58 includes a second backup copy 120b of main circuit board's PID data set 120. Further details regarding the storage, retrieval, and usage of these backup copies 120a and 120b are provided below.

Battery charger controller 106 is, in the illustrated embodiment of FIG. 5, adapted to store at least two data sets in its memory 110. These two data sets include a battery charger board data set 122, and the first backup copy 120a of the main circuit board's PID data set 120. Battery charger board data set 122 includes a battery charger circuit board Product ID (PID) data subset 130, a battery charger circuit board fault tracking data subset 132, and a battery charger circuit board statistics data subset 134. Battery charger circuit board PID data subset 130 include similar data to what is found in main product ID data set 120, except this data is specifically tailored to battery charger circuit board 56 rather than to main circuit board 54. That is, battery charger circuit board PID data subset 130 includes five identifiers: (1) a software identifier indicating what version of software is installed on battery charger circuit board 56; (2) a circuit board serial number that uniquely identifies battery charger circuit board 56; (3) a product part number that identifies what part of patient support apparatus 20 battery charger circuit board 56 is; (4) a product serial number that uniquely identifies the particular patient support apparatus 20 into which battery charger circuit board 56 is integrated; and (5) a hardware version that identifies the particular hardware version that is currently installed on battery charger circuit board 56. It will be understood that the precise contents of the battery charger circuit board product ID data subset 130 may be varied, including further additions to the aforementioned data, omissions of one or more of these data items, and/or a combination of both additions and omissions.

As with main controller 100, in some embodiments, battery charger controller 106 stores these five data items— the software identifier, circuit board serial number, product part number, product serial number, and hardware version— in a file, and concurrently generates an error-detecting code for that file so that the contents of that file can be checked for accuracy. Although other types of error detecting codes may be used, in at least one embodiment, battery charger controller 106 is programmed to generate a 16 bit Cyclical Redundancy Check (CRC) that accompanies the file containing the five data items mentioned above. The sixteen bit CRC number is stored along with, and in some cases as part of, the battery charger circuit board PID data subset 130. Whenever the contents of any of the five data items mentioned above are changed, battery charger controller 106 generates a new CRC value for the updated data and stores it in memory 110. Further, whenever the contents of the file containing these five data items are retrieved (e.g. read), controller 106 is programmed to examine the CRC value and the contents of file read from memory 110 to determine if there is any error with the retrieved. This error checking is done in the same manner discussed above with respect to main controller 100, although other manners of error-checking may be used.

In addition to battery charger board PID data subset 130, battery charger controller 106 also stores fault tracking data subset 132 and statistics data subset 134 in memory 110 (FIG. 5). Both of these data subsets 132 and 134 are populated and updated by battery charger controller 106 during operation of patient support apparatus 20. Battery charger controller 106 stores faults that it detects during its operation in data subset 132 and stores statistical information that it generates during operation in data subset 134. Although other types of data may be stored in data subset 132, in at least one embodiment, battery charger controller 106 is adapted to store any one or more of the following types of data in data subset 132: an ID of the detected fault, a snapshot of data gathered during a time window adjacent the detection of the fault, an active counter of the number of faults detected, a time stamp of when faults were detected and/or activated, a time stamp of when faults were inactivated, an indicator of what faults, if any, are currently active, and the like. Additionally, although other types of data may be stored in data subset 134, in at least one embodiment of patient support apparatus 20, battery charger controller 106 is adapted to store any one or more of the following types of data in data subset 134: number of charge cycles of battery 60, average charging time, current charge capacity, average drain time, maximum amperage, average amperage, and the like. This data is repetitively gathered and updated by battery charger controller 106 during the operation of patient support apparatus 20.

In addition to storing battery charger circuit board data set 122 in memory 110, battery charger controller 106 is configured to send a copy of this data set to main circuit board 54 during the operation of patient support apparatus 20. This copy is received by main controller 100 and written into memory 104. This copy is identified in FIG. 5 by the reference number 122a. In at least one embodiment, battery charger controller 106 sends the updates to the data within data set 122 to main circuit board 54 in real time so that main controller 100 can store them in memory 104 as they occur. In some embodiments, battery charger controller 106 also writes these updates to memory 110 in real time. However, in at least one alternative embodiment, in order to reduce the number of read and write cycles experienced by memory 110 (particularly if memory 110 has a relatively low number of useful read and write cycles, such as some forms of flash memory), battery charger controller 106 is configured to only update the data within data set 122 at certain times. The trigger for these write cycles to memory 110 may vary. In some embodiments, battery charger controller 106 is configured to update the data within data set 122 whenever patient support apparatus 20 is about to go into a sleep mode.

In other embodiments, this trigger may be modified to be based on a periodic time period, the amount of accumulated data that needs to be updated, and/or a combination of these and/or other factors. The accumulated data that needs to be updated may be stored in a volatile memory (e.g. RAM) on battery charger circuit board 56 while controller 106 awaits the triggering event for transferring it to memory 110.

As will be discussed in greater detail below, regardless of the event that triggers the updating of data set 122 by battery charger controller 106, battery charger controller 106 sends a backup copy of this data to main circuit board 54 for storage so that, in the event battery charger circuit board 56 is replaced or detects errors in any of the data in data set 122, it can retrieve that data by requesting main controller 100 to resend back to it the contents of data set 122a stored in main circuit board's memory 104. In this manner, data generated and stored by battery charger circuit board 56 during the course of its lifetime is backed up and can be automatically restored to it if it detects any corruption in that data, and/or can be automatically transferred to a newly installed battery charger circuit board 56. In the latter case, the data generated and stored by a previously installed battery charger circuit board 56 is automatically transferred to a newly installed battery charger circuit board 56 without requiring the technician, or other person installing the new battery charger circuit board 56, to take any manual steps to ensure that this historical data is transferred to the new battery charger circuit board 56.

Similar to the error-checking process described above with respect to main controller 100, battery charger controller 106 is configured, in at least some embodiments, to generate an error detecting code not only for its PID data subset 130, but also for its fault tracking data subset 132 and its statistics data subset 134. The error detecting codes may be the same as the one used for data subset 130 (e.g. a sixteen bit CRC value). These values are used by battery charger controller 106 to determine if there are any errors in the data contained within the files of data subsets 132 and/or 134. Battery charger controller 106 also updates these CRC values whenever the contents of these data subset are changed, and forwards the updated CRC values to main controller 100 (or alternatively, main controller 100 generates the CRC values at its end when storing the backup copy 122a in memory 104).

As was briefly discussed previously, battery charger controller 106 also stores a first backup copy 120a of the main circuit board's PID data set 120 in its memory 110 (FIG. 5). The contents of this backup copy 120a are sent back to main circuit board 54 at times during the operation of patient support apparatus 20 in order to accomplish at least two different functions, both of which will be discussed in greater detail below. The first function is for main circuit board 54 to determine which, if any, of the circuit boards 54 are new circuit boards that have replaced a previously installed circuit board, and the second function is to use this backup copy of data 120a to populate any missing or incorrect data contained within data set 120 if main circuit board 54 determines that it is a new replacement for a previously installed main circuit board 54.

Actuator controller 112 is, in the illustrated embodiment of FIG. 5, adapted to store at least two data sets in its memory 116. These two data sets include an actuator control circuit board data set 124, and the second backup copy 120b of the main circuit board's PID data set 120. Actuator control circuit board data set 124 includes an actuator control circuit board Product ID (PID) data subset 140, an actuator control circuit board fault tracking data subset 142, an actuator control circuit board statistics data subset 144, and an actuator calibration data subset 146. Actuator control circuit board PID data subset 140 includes similar data to what is found in both main product ID data set 120 and battery charger circuit board PID data subset 130, except this data is specifically tailored to actuator control circuit board 58 rather than to main circuit board 54 and battery charger circuit board 56. That is, actuator control circuit board PID data subset 140 includes five identifiers: (1) a software identifier indicating what version of software is installed on actuator control circuit board 58; (2) a circuit board serial number that uniquely identifies actuator control circuit board 58; (3) a product part number that identifies what part of patient support apparatus 20 actuator control circuit board 58 is; (4) a product serial number that uniquely identifies the particular patient support apparatus 20 into which actuator control circuit board 58 is integrated; and (5) a hardware version that identifies the particular hardware version that is currently installed on actuator control circuit board 58. It will be understood that the precise contents of the actuator control circuit board PID data subset 140 may be varied, including further additions to the aforementioned data, omissions of one or more of these data items, and/or a combination of both additions and omissions.

As with main controller 100, in some embodiments, actuator controller 112 stores these five data items—the software identifier, circuit board serial number, product part number, product serial number, and hardware version—in a file, and concurrently generates an error-detecting code for that file so that the contents of that file can be checked for accuracy. Although other types of error detecting codes may be used, in at least one embodiment, actuator controller 112 is programmed to use the same error detecting codes used by the other circuit boards and controller 100 and 106 discussed above (e.g. a 16 bit Cyclical Redundancy Check (CRC)). When used, the sixteen bit CRC number is stored along with, and in some cases as part of, the actuator control circuit board PID data subset 140. Whenever the contents of any of the five data items mentioned above are changed, actuator controller 112 generates a new CRC value for the updated data and stores it in memory 116. Further, whenever the contents of the file containing these five data items are retrieved (e.g. read), controller 112 is programmed to examine the CRC value and the contents of the associated file read from memory 116 to determine if there is any error with the retrieved file. This error checking is done in the same manner discussed above with respect to main controller 100, although other manners of error-checking may be used.

In addition to actuator control circuit board PID data subset 140, actuator controller 112 also stores fault tracking data subset 142, statistics data subset 144, and calibration data 146 in memory 116 (FIG. 5). Data subsets 142 and 144 are populated and updated by actuator controller 112 during operation of patient support apparatus 20, and data subset 146 is populated and updated whenever any of the components in direct communication with actuator control circuit board 58 are calibrated and/or recalibrated (e.g. lift motor 62). Actuator controller 112 stores faults that it detects during its operation in data subset 142 and stores statistical information that it generates during operation in data subset 144. Although other types of data may be stored in data subset 142, in at least one embodiment, actuator controller 112 is adapted to store any one or more of the following types of data in data subset 142: an ID of the detected fault, a snapshot of data gathered during a time window adjacent the detection of the fault, an active counter of the number of faults detected, a time stamp of when faults were detected and/or activated, a time stamp of when faults were inactivated, an indicator of what faults, if any, are currently active, and the like.

Additionally, although other types of data may be stored in data subset 144, in at least one embodiment of patient support apparatus 20, actuator controller 112 is adapted to store any one or more of the following types of data in data subset 144: total hours that lift motor 62 has operated; the total hours which lift motor 62 has operated with a low load; the total hours lift motor 62 has operated with a medium load; the total hours lift motor 62 has operated with a heavy load; the total hours lift motor 62 has operated with more than a heavy load; the maximum amperage drawn by lift motor 62; the average amps drawn by lift motor 62 with the low load; the average amps drawn by lift motor 62 with the medium load; the average amps drawn by lift motor 62 with the heavy load; and the average amps drawn by lift motor 62 with the more than heavy load. This data is repetitively gathered and updated by actuator controller 112 during the operation of patient support apparatus 20.

Actuator controller 112 also stores calibration data in data subset 146 (FIG. 5). Although other types of calibration data may be stored in data subset 146, actuator controller 112 is adapted, in at least one embodiment, to store any one or more of the following types of data in subset 146: a maximum height, a load height, a transport height, a position window, a transport window, and the like.

In addition to storing actuator control circuit board data set 124 in memory 116, actuator controller 112 is configured to send a copy of this data set 124 to main circuit board 54 during the operation of patient support apparatus 20. This copy is received by main controller 100 and written into memory 104. This copy is identified in FIG. 5 by the reference number 124a. In at least one embodiment, actuator controller 112 sends the updates to the data within data set 124 to main circuit board 54 in real time so that main controller 100 can store them in memory 104 as they occur. In some embodiments, actuator controller 112 also writes these updates to memory 116 in real time. However, in at least one alternative embodiment, in order to reduce the number of read and write cycles experienced by memory 116 (particularly if memory 116 has a relatively low number of useful read and write cycles, such as some forms of flash memory), actuator controller 112 is configured to only update data set 124 within memory 116 at certain times. The trigger for these write cycles to memory 116 may vary. In some embodiments, actuator controller 112 is configured to update the data within data set 124 whenever patient support apparatus 20 is about to go into a sleep mode. In other embodiments, this trigger may be modified to be based on a periodic time period, the amount of accumulated data that needs to be updated, and/or a combination of these and/or other factors. The accumulated data that needs to be updated may be stored in a volatile memory (e.g. RAM) on actuator control circuit board 58 while controller 112 awaits the triggering event for transferring it to memory 116.

As will be discussed in greater detail below, regardless of the event that triggers the updating of data set 124 by actuator controller 112, actuator controller 112 sends a backup copy of this data to main circuit board 54 for storage so that, in the event actuator control circuit board 58 is replaced or detects errors in any of the data in data set 124, it can retrieve that data by requesting main controller 100 to resend back to it the contents of data set 124a stored in main circuit board's memory 104. In this manner, data generated and stored by actuator control circuit board 58 during the course of its lifetime is backed up and can be automatically restored to it if it detects any corruption in that data, and/or can be automatically transferred to a newly installed actuator control circuit board 58. In the latter case, the data generated and stored by a previously installed actuator control circuit board 58 is automatically transferred to a newly installed actuator control circuit board 58 without requiring the technician, or other person installing the new actuator control circuit board 58, to take any manual steps to ensure that this historical data is transferred to the new actuator control circuit board 58.

Similar to the error-checking processes described above with respect to main controller 100 and battery charger controller 106, actuator controller 112 is configured, in at least some embodiments, to generate an error detecting code not only for its PID data subset 140, but also for its fault tracking data subset 142, its statistics data subset 144, and its calibration data subset 146. The error detecting codes may be the same as the one used for data subset 140 (e.g. a sixteen bit CRC value). These values are used by actuator controller 112 to determine if there are any errors in the data contained within the files of data subsets 142, 144 and/or 146. Actuator controller 112 also updates these CRC values whenever the contents of these data subsets are changed, and forwards the updated CRC values to main controller 100 (or alternatively, main controller 100 generates the CRC values at its end when storing the backup copy 124*a* in memory 104).

As was briefly discussed previously, actuator controller 112 (FIG. 5) also stores a second backup copy 120*b* of the main circuit board's PID data set 120 in its memory 116. The contents of this backup copy 120*b* are sent back to main circuit board 54 at times during the operation of patient support apparatus 20 in order to accomplish at least two different functions, both of which will be discussed in greater detail below. The first function is for main circuit board 54 to determine which, if any, of the circuit boards 54 are new circuit boards that have replaced a previously installed circuit board, and the second function is to use this backup copy data 120*b* to populate any missing or incorrect data contained within data set 120 if main circuit board 54 determines that it is a new replacement for a previously installed main circuit board 54.

Figure 6:
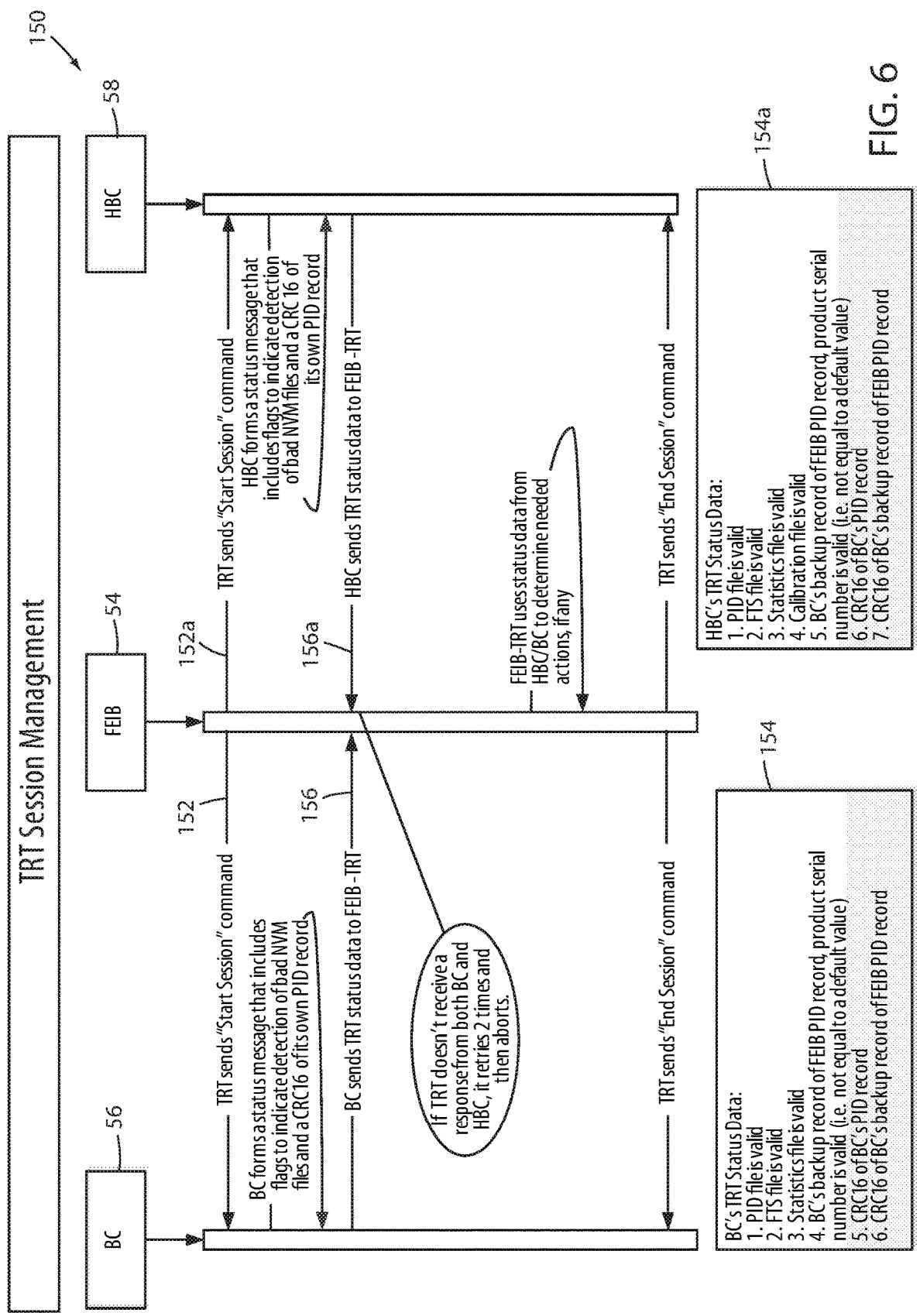
FIG. 6 is a diagram of the general communication between the circuit boards of the patient support apparatus of FIG. 1.

FIG. 6 illustrates in greater detail a communication algorithm 150 followed by control system 52 in order to carry out the general communications between circuit boards 54, 56, and 58 (and 86, if included). These general communications are used for, among other purposes, automatically detecting if any of circuit boards 54, 56, and/or 58 (and 86, if included) are newly installed circuit boards that have replaced a previously installed circuit board. These communications are also used to populate the memory of any newly installed circuit board with the historical data gathered by the previously installed circuit board. Still further, these communications are used to detect if any data is corrupt, and if so, to replace that data with uncorrupted backup data.

Communication algorithm 150 (FIG. 6) is executed by circuit boards 54, 56, and 58 (and 86, if present), and more specifically by the respective controllers on these circuit boards. Communication algorithm 150 begins when main controller 100 sends a start session command at step 152 to battery charger circuit board 56 over communication bus 72. The command is received by battery charger controller 106 and instructs battery charger controller 106 to prepare a status message 154 to be sent back to main controller 100. The contents of status message 154 are illustrated in FIG. 6 and include the six items shown therein. These items are the following: (1) an indication of whether the battery charger PID file (contained within data subset 130 of memory 110) is valid, which controller 106 determines by using the CRC value associated with data subset 130; (2) an indication of whether the fault tracking file (contained within data subset 132 of memory 110) is valid, which controller 106 determines by using the CRC value associated with data subset 132; (3) an indication of whether the statistics file (contained within the data subset 134 of memory 110) is valid, which controller 106 determines by using the CRC value associated with data subset 134; (4) an indication of whether the first backup copy of the main circuit board's PID file (contained with the first backup copy of the main circuit board's PID data set 120*a*) is valid, which controller 106 determines by using the CRC value associated with data set 120*a*; (5) the CRC value corresponding to the data subset 130; and (6) the CRC value corresponding to the first backup copy of the main circuit boards' PID data set 120*a* stored within memory 110.

At step 156 (FIG. 6), battery charger controller 106 forwards the status message 154 to main controller 100 via communication bus 72 (through transceivers 108 and 102). Main controller 100 processes this status message 154 in a manner that will be discussed in greater detail below. If main controller 100 does not receive status message 154 within a threshold amount of time, it resends the start session command requesting the message (step 152) and waits for the status message. In some embodiments, this is repeated one or more times until status message 154 is received. If status message 154 is not received within a threshold number of attempts and/or within a threshold amount of time, main controller 100 terminates the attempts and may, in some embodiments, issue an error notification to the user.

Steps 152 and 156 are repeated by main controller 100 for communications with actuator control circuit board 58. These steps are identified in FIG. 6 with the reference numbers 152*a* and 156*a*. Step 152*a* is the same as step 152 except that main controller sends the request of step 152*a* to actuator control circuit board 58, rather than battery charger circuit board 56. In response to this request, actuator controller 112 responds with a status message 154*a* that it sends back to main controller 100 at step 156*a*. Status message 154*a* contains the same type of data as status message 154, except instead of data relating to battery charger circuit board 56, it includes data relating to actuator control circuit board 58. Additionally, actuator controller 112 populates status message 154*a* with an indication of whether the calibration file (contained within the data subset 146 of memory 116) is valid, which controller 112 determines by using the CRC value associated with data subset 146. As with status message 154, if main controller 100 does not receive status message 154*a* within a threshold number of attempts and/or within a threshold amount of time, main controller 100 terminates the attempts and may, in some embodiments, issue an error notification to the user.

In some embodiments, the trigger for starting algorithm 150 is any one or more of the following three actions, as detected by main controller 100: (1) power is initially turned on or supplied to patient support apparatus 20; (2) patient support apparatus 20 awakens from a sleep mode; or (3) an external diagnostics tool has been connected and disconnected from patient support apparatus 20 (e.g. via USB port 78). It will be understood that main controller 100 can be modified to execute algorithm 150 based on one or more other triggers, either alone or in combination with any of these three triggers. Such other triggers may include the passage of a predetermined amount of time, the location of patient support apparatus 20, the connection of patient support apparatus 20 to a cot fastening system (either physically or communicatively), or still other triggers.

Figure 7:
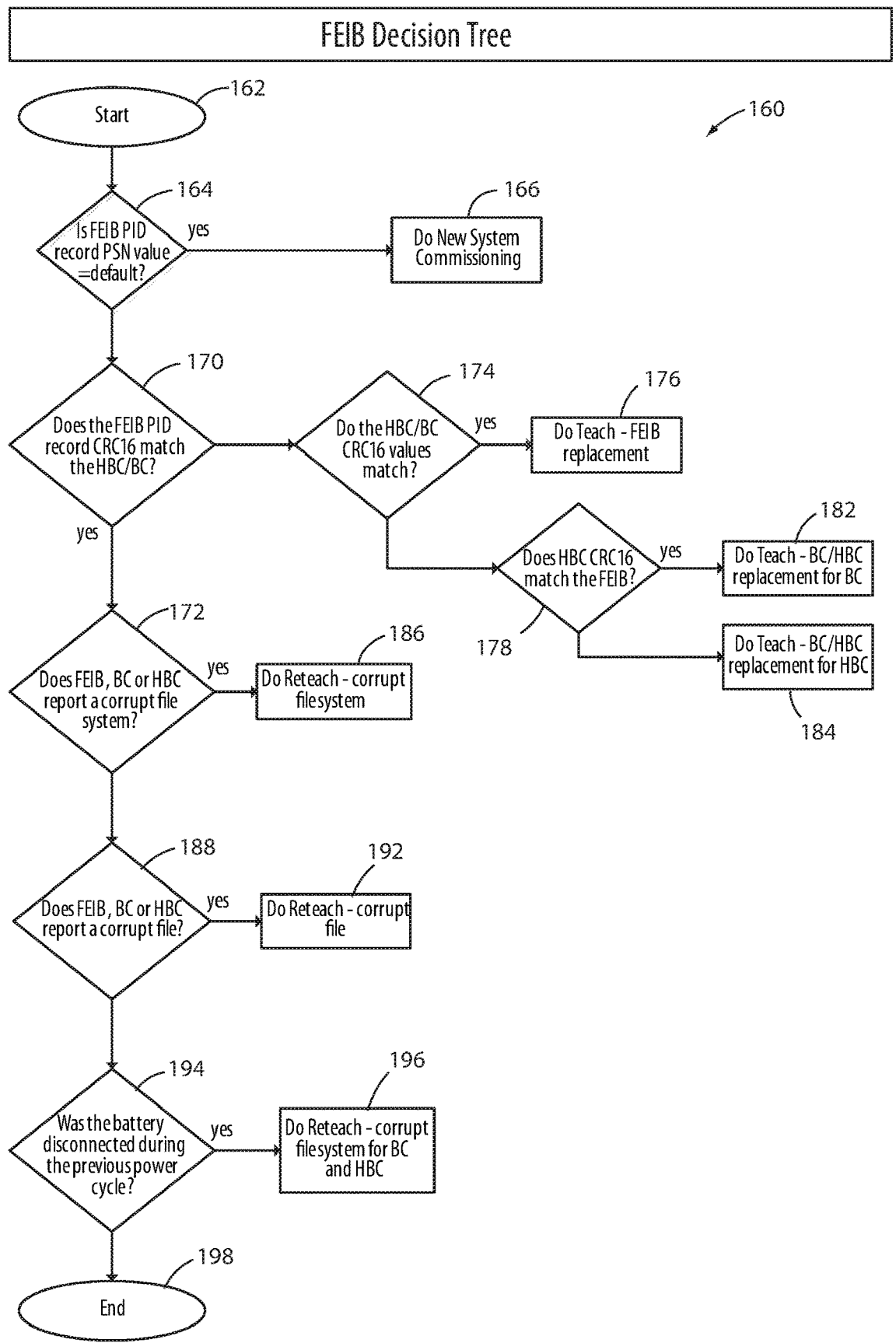
FIG. 7 is a flow diagram of a new circuit board and corrupt data detection algorithm executed by the main circuit board of the patient support apparatus of FIG. 1.

FIG. 7 illustrates one example of a board replacement and error detection algorithm 160 executed by main controller 100. Algorithm 160 starts at step 162 after receiving the status messages 154 and 154a at steps 156 and 156a, respectively. After starting at step 162, main controller 100 proceeds to step 164 where it examines the contents of its main circuit board PID data set 120 that is stored within its memory 104. Specifically, it looks for the value of the product serial number contained within data set 120. If that product serial number is equal to a default value, main controller 100 concludes that patient support apparatus 20 is newly manufactured. This is because all main circuit boards 54 are configured to utilize a default value for the product serial number until they are manually assigned the actual product serial number corresponding to the particular patient support apparatus 20 into which they are incorporated. Once the patient support apparatus 20 is assigned its unique serial number during the manufacturing process (or after the manufacturing process), main controller 100 receives the unique (and non-default) serial number and stores it in data set 120 (and thus overwrites the default value). The unique serial number may be communicated to main circuit board 54 either via USB port 78 or wireless communication circuit board 86.

Figure 8:
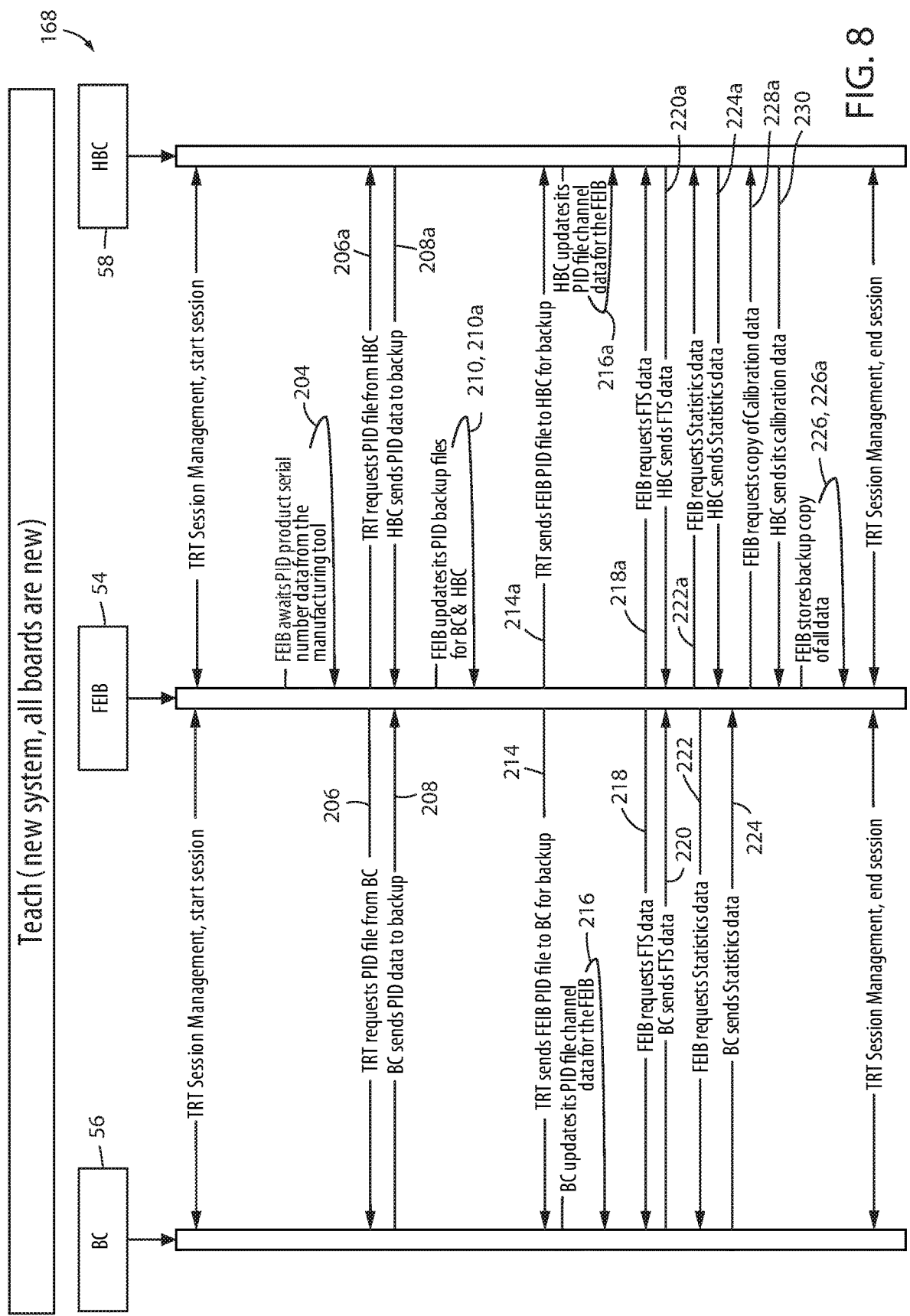
FIG. 8 is a diagram of a new product commissioning algorithm executed by the patient support apparatus of FIG. 1 after the patient support apparatus is manufactured and circuit boards are initially installed on the patient support apparatus.

If main controller 100 determines at step 164 (FIG. 7) that the product serial number contained within data set 120 is the default value, it concludes that patient support apparatus 20 has been newly manufactured and not yet commissioned. In response, it proceeds to step 166 where it performs a new product commissioning algorithm 168. The details of new product commissioning algorithm 168 are illustrated in FIG. 8 and discussed in greater detail below.

If main controller 100 determines at step 164 (FIG. 7) that the product serial number contained within data set 120 is not a default value, it concludes that patient support apparatus 20 has previously been commissioned and proceeds to step 170. At step 170, main controller 100 begins the process of determining if any of the circuit boards 54, 56, and 58 (and 86, if present) are replacements of previously installed circuit boards. This process begins at step 170 when main controller 100 compares the CRC value associated with the main circuit board PID data set 120 and stored in memory 104 with the CRC values corresponding to the first and second backup copies 120a and 120b of data set 120 (which are stored, respectively, in memories 110 and 116). As was noted above with respect to communications algorithm 150, the CRC values corresponding to first and second backup copies 120a and 120b stored in memories 110 and 116, respectively, are sent to main controller within messages 154 and 154a, respectively. Thus, at step 170, main controller 100 compares the CRC value in its own local memory 104 associated with data set 120 to the CRC values it receives from circuit boards 56 and 58 that are associated with the backup copies 120a and 120b. If all three of the CRC values match each other, then main controller 100 concludes that none of the circuit boards 54, 56, and 58 are replacements that have been installed since the last time algorithm 160 was executed. Main controller 100 thereafter proceeds to step 172.

If any of the three CRC values compared at step 170 (FIG. 7) do not match each other, this is interpreted by main controller 100 to indicate that one of the circuit boards 54, 56, or 58 (or 86, if included) has been recently replaced. (The term "recent" in this context refers to being replaced at some point since that last time algorithm 160 was executed by controller 100). If controller 100 concludes at step 170 that a board has been recently replaced, it proceeds to step 174 where it determines which one of the circuit boards is the recent replacement board. At step 174, main controller 100 determines if the CRC values for data sets 120a and 120b received from circuit boards 56 and 58 match each other. If they do match each other, main controller 100 concludes that main circuit board 54 has been recently installed as a replacement for a previous main circuit board. This conclusion is justified because, when a new main circuit board 54 is installed, it will not initially include a data set 120 that matches the data sets 120a and 120b stored in circuit boards 56 and 58. Instead, the data sets 120a and 120b stored on circuit boards 56 and 58 will be copies of the data received from the previously installed main circuit board. Main controller 100 will therefore proceed to step 176 where it follows a main circuit board replacement algorithm 180. The details of main circuit board replacement algorithm are discussed in greater detail below with respect to FIG. 9.

If main controller 100 concludes at step 174 that the CRC values for data sets 120a and 120b received from circuit boards 56 and 58 do not match each other, it proceeds to step 178. At step 178, main controller 100 determines if the battery charger circuit board 56 is a recently installed replacement for a previously installed battery charger circuit board, or if the actuator control circuit board 58 is a recently installed replacement for a previously installed actuator control circuit board 58. Main controller 100 makes this decision in the following manner: if the CRC value associated with data set 120a (stored in memory 110) matches the CRC value associated with data set 120 (stored in memory 104), main controller 100 concludes that actuator control circuit board 58 has recently replaced a previously installed actuator control circuit board 58. On the other hand, if the CRC value associated with data set 120b (stored in memory 116) matches the CRC value associated with the data set 120 (stored in memory 104), main controller 100 concludes that the battery charger circuit board 56 has recently replaced a previously installed battery charger circuit board 56.

Main controller 100 follows the aforementioned decision logic at step 178 because, whenever a new actuator control circuit board 58 is initially installed, it will not yet have received the second backup copy 120b of the main circuit board's PID data set 120 and stored it in memory 116. Thus, backup copy 120b will either be empty, or it will contain different data. In either event, the CRC value associated with backup copy 120b will not match the CRC value associated with the original data set 120 stored in memory 104 of main circuit board 54. Accordingly, when main controller 100 determines at step 178 that the CRC value of second backup copy 120b of the main circuit board's PID data set 120 stored in memory 116 does not match the CRC values associated with data set 120 (stored in memory 104) and data set 120a (stored in memory 110), this is the result of actuator control circuit board 58 having been recently installed and not yet having the correct second backup data set 120b.

The same reasoning applies to the decision by main controller 100 at step 178 that the battery charger circuit board 56 is a newly installed replacement of a previously installed battery charger circuit board 56. That is, whenever a new battery charger circuit board 56 is initially installed, it will not yet have received the first backup copy 120a of the main circuit board's PID data set 120 and stored it in memory 110. Thus, first backup copy 120a will either be empty, or it will contain different data. In either event, the CRC value associated with backup copy 120a will not match the CRC value associated with the original data set 120 stored in memory 104 of main circuit board 54. Accordingly, when main controller 100 determines at step 178 that the CRC value of first backup copy 120*a* of the main circuit board's PID data set 120 stored in memory 110 does not match the CRC values associated with data set 120 (stored in memory 104) and data set 120*b* (stored in memory 116), this is the result of battery charger circuit board 56 having been recently installed and not yet having the correct first backup data set 120*a*.

From step 178 of algorithm 160 (FIG. 7), main controller 100 proceeds to either step 182 or step 184. It proceeds to step 182 if it determines at step 178 that the battery charger circuit board 56 is a recent replacement for a previously installed battery charger circuit board. On the other hand, main controller proceeds from step 178 to step 184 if it determines at step 178 that the actuator control circuit board 58 is a recent replacement for a previously installed actuator control circuit board. At both steps 182 and 184, main controller 100 follows a replacement board algorithm 190 that is described in more detail below with respect to FIG. 10.

Returning to step 170 of algorithm 160, main controller 100 proceeds from step 170 to step 172 if it determines at step 170 that none of the circuit boards 54, 56, or 58 (or 86, if present) are recent replacements of previously installed circuit boards. At step 172, main controller 100 determines if any of the circuit boards have a corrupt file system. Main controller 100 does this for main circuit board 54 by using the CRC values of the files stored in its local memory 104 to determine if any of those files contain errors. This may be accomplished in any conventional manner of using CRC codes for checking data integrity, such as, for example, the two previously mentioned methods (e.g. reading the files in memory 104 and using them to calculate new CRC values and comparing them to the stored CRC values; or generating a new CRC from the combination of the files and their associated CRC values and comparing the new CRC values to expected residue constants).

If main controller 100 determines at step 172 (FIG. 7) that multiple ones of the files stored in any of data sets 120, 122*a*, or 124*a* contain corrupt data (as determined from their CRC values), it proceeds to step 186. If main controller 100 determines that only a single one of, or none of, the files stored in data sets 120, 122*a*, and 124*a* contain corrupt data, it proceeds to determine whether there are any corrupt file systems onboard battery charger circuit board 56 or actuator control circuit board 58. The determination whether battery charger circuit board 56 contains a corrupt file system is made by battery charger controller 106 and reported to main controller 100 as part of status message 154.

Similarly, the determination of whether actuator control circuit board 58 contains a corrupt file system is made by actuator controller 112 and reported to main controller 100 as part of status message 154*a*. Accordingly, main controller 100 is able to determine at step 172 if either battery charger circuit board 56 or actuator control circuit board 58 contain a corrupt file system simply by examining the contents of status messages 154 and 154*a*. If neither of these circuit boards 56 nor 58 contain a corrupt file system (and main circuit board 54 also does not contain a corrupt file system), main controller 100 proceeds to step 188. On the other hand, if any one of circuit boards 54, 56, or 58 (or 96, if present) contain a corrupt file system, main controller 100 proceeds to step 186. At step 186, main controller 100 executes a corrupted file system replacement algorithm 200*a* or 200*b*, depending upon which circuit board contains the corrupted file system. Algorithms 200*a* and 200*b* are described in greater detail below with respect to FIGS. 11 & 12, respectively.

Returning to step 172, battery charger controller 106 and actuator controller 112 determine if their respective boards contain a corrupt file system in the same manner that main controller 100 determines if its local file system (saved in memory 104) is corrupt. That is, prior to sending status message 154 at step 156, battery charger controller 106 uses the CRC values of the files stored in its local memory 110 to determine if any of those files contain errors. This may be accomplished in any conventional manner of using CRC codes for checking data integrity, such as the examples mentioned above, or in other manners. If more than one file is determined to be corrupt, battery charger controller 106 concludes that its file system is corrupt and reports this file system corruption to main controller in message 154. If only a single file is determined to be corrupt, battery charger controller 106 concludes that its file system is not corrupt, but instead reports that only a single file is corrupt in message 154 (and main controller 100 uses this information in step 188, as discussed more below). If battery charger controller 106 concludes that no files are corrupt, it also reports this information in status message 154.

Actuator controller 112 operates in a similar manner. That is, prior to sending status message 154*a* at step 156*a*, actuator controller 112 uses the CRC values of the files stored in its local memory 116 to determine if any of those files contain errors. This may be accomplished in any conventional manner of using CRC codes for checking data integrity, such as the examples mentioned above, or in other manners. If more than one file is determined to be corrupt, actuator controller 112 concludes that its file system is corrupt and reports this file system corruption to main controller in message 154*a*. If only a single file is determined to be corrupt, actuator controller 112 concludes that its file system is not corrupt, but instead reports that only a single file is corrupt in message 154*a* (and main controller 100 uses this information in step 188, as discussed more below). If actuator controller 112 concludes that no files are corrupt, it also reports this information in status message 154*a*.

In summary, main controller 100 executes step 172 (FIG. 7) by examining its own files stored in local memory 104 to determine if more than one is corrupt, and concluding its file system is corrupt if there are more than one corrupt files. It determines if the files system of circuit boards 56 and 58 are corrupt by examining the contents of status messages 154 and 154*a*, respectively, which both contain the results of the file corruption detection actions undertaken by controller 106 and 112, respectively. If no file systems are corrupt, main controller proceeds to step 188. If any circuit board has a corrupt file system, main controller 100 proceeds to step 186 and executes one of the corrupted file system replacement algorithms 200*a* or 200*b*, which are discussed below with respect to FIGS. 11 & 12.

At step 188 (FIG. 7), main controller 100 determines whether any single corrupted files exist on main circuit board 54, battery charger circuit board 56, and actuator control circuit board 58 (and communications board 86, if present). Main controller 100 determines this using the results of its analysis performed during step 172. That is, main controller 100 determines that a corrupt file exists if it detects one onboard main circuit board 54, if battery charger circuit board 56 reports the existence of one onboard battery charger circuit board 56 in status message 154, or if actuator control circuit board 58 reports the existence of one onboard actuator control circuit board 58 in status message 154*a*. If any corrupted file is detected, main controller 100 proceeds to step 192 where it executes a corrupted file replacement algorithm 212*a* or 212*b*, depending upon which circuit board the corrupted file is located. Corrupt file replacement algorithms 212*a* and 212*b* are discussed in greater detail below with respect to FIGS. 13 & 14, respectively. If no corrupted files are detected at step 188, main controller 100 proceeds to step 194.

At step 194 (FIG. 7), main controller 100 determines if battery 60 was disconnected during the previous power cycle. Main circuit board 54, in at least some embodiments, is configured to include a capacitive power supply that continues to provide electrical power to the main circuit board 54 for a predetermined minimum amount of time after battery 60 is disconnected, or electrical power is otherwise cut off. This predetermined minimum amount of time is sufficient for main controller 100 to write any data it has temporarily stored in its volatile memory (e.g. RAM) into non-volatile memory 104. This data includes updates received from either of circuit boards 56 or 58 to any of the data sets 122 or 124. As a result of this temporary capacitive power supply (which may be provided by one or more capacitors), main controller 100 is able to record data updates in its non-volatile memory 104 that may not have been recorded in the non-volatile memories 110 or 116 (as noted previously, in some embodiments, controllers 106 and 112 do not update the data in their memories 110, 116 in real time in order to reduce the write cycles of these memories (particularly if they are flash memories with low write cycle ratings), but instead only update these memories at certain designated times (e.g. before entering a sleep cycle)). If control system 52 is designed in this manner, it is possible that, when power is terminated to patient support apparatus 20 in a non-controlled manner, memories 110 and 116 may not contain the most recently updated set of data, but instead such data may be found in the backup copies 122*a* and 124*a* stored on main circuit board 54.

Main controller 100 therefore detects at step 194 if the battery was disconnected in the previous power cycle in order to determine whether the memories 110 and/or 116 may need to be updated with the most recent data that was recorded in main memory 104, but not in memories 110 and/or 116. If main controller detects at step 194 that the battery was disconnected during the previous power cycle, it proceeds to step 196. If it does not detect that the battery was disconnected during the previous power cycle, it proceeds to step 198, where it ends the performance of algorithm 160. As noted, main controller 100 will restart algorithm 160 when it is re-triggered, which may be due to any of the reasons mentioned previously (e.g. control system 52 awakens from the sleep mode, power is cycled off and on, and/or a diagnostic tool is connected and disconnected from control system 52). Main controller 100 may determine if power has been disconnected during the previous power cycle in any conventional manner, such as, by examining a state of a relay and/or a memory cell in memory 104 in which main controller 100 inputs data indicating a power disconnection whenever battery 60 power is terminated and it is operating on capacitor power. When main controller 100 proceeds to step 196, it executes the corrupt file system replacement algorithm 200*b*, which is described in more detail below with respect to FIG. 12.

Before turning to FIG. 8, it will be noted that many modifications can be made to algorithm 160. These include, for example, comparing more than just the CRC values of the various data sets when determining if a circuit board has been replaced. In other words, although steps 170, 174, and 178 have been described above as comparing the CRC values from different circuit boards that normally match each other, this may be changed to a comparison of the actual data that is encoded with the CRC values, or some portion of that data. In the embodiment described above, main controller 100 uses 16 bit CRC value comparisons because this reduces the traffic on communications bus 72. If the bandwidth of communication bus 72 is not a concern, algorithm 160 may be modified to instruct main controller 100 to compare more than just the CRC values of the various data sets and/or subsets in order to determine discrepancies between the data and its backup copies.

FIG. 8 illustrates one example of the new product commissioning algorithm 168. As was noted previously, main controller 100 (in conjunction with battery charger controller 106 and actuator controller 112) is configured to execute algorithm 168 in response to a determination at step 166 (FIG. 7) that patient support apparatus 20 is a newly commissioned patient support apparatus. Main controller 100 starts algorithm 168 at a step 204 where it awaits the receipt of a unique product serial number from a tool used by the manufacturer of patient support apparatus 20. The tool may be a laptop computer connected to patient support apparatus 20 via USB port 78 or wirelessly via wireless communication circuit board 86. Alternatively, the tool may be another type of computer or other electronic device that is able to communicate a unique serial number for that particular patient support apparatus 20 to main controller 100. Regardless of the specific type of tool used to communicate the unique serial number, controller 100 stores the unique serial number in its main board PID data set 120 and overwrites the default value that was previously stored therein.

At step 206 (FIG. 8), main controller 100 sends a request to battery charger circuit board 56 requesting that battery charger controller 106 send it a copy of its PID data subset 130. Stated alternatively, main controller 100 requests a backup copy 130*a* from battery charger circuit board 56 at step 206. Prior to this request, main circuit board 54 does not contain the backup copy 130*a* (see FIG. 5) in its memory 104. At step 208, battery charger controller 106 sends the backup copy 130*a* to main circuit board 54. At step 210, main controller 100 stores this backup copy 130*a* in its memory 104.

At step 214, main controller 100 sends the first copy 120*a* of its main PID data set 120 to battery charger circuit board 56. After receipt of this first copy 120*a*, battery charger controller 106 stores this first copy 120*a* in its local memory 110 at step 216. Prior to the receipt of this first copy 120*a*, battery charger circuit board 56 does not contain the first backup copy 120*a* (see FIG. 5) in its memory 110.

At step 218 (FIG. 8), main controller 100 sends a request to battery charger controller 106 requesting a backup copy 132*a* of the battery charger circuit board fault tracking data subset 132. Prior to the receipt of this backup copy 132*a*, main circuit board 54 does not contain a backup copy 132*a* of battery charger circuit board 56's fault tracking data subset 132. The backup copy 132*a* is sent to main controller 100 at step 220.

At step 222 (FIG. 8), main controller 100 sends a request to battery charger controller 106 requesting a backup copy 134*a* of the battery charger circuit board statistics data subset 134. Prior to the receipt of this backup copy 134*a*, main circuit board 54 does not contain a backup copy 134*a* of battery charger circuit board 56's statistics data subset 134. The backup copy 134*a* is sent to main controller 100 at step 224.

At step 226, main controller 100 stores all of the backup copies of data it has received from battery charger circuit board 56 in its local memory 104. These backup copies include backup copies of data subsets 130*a*, 132*a*, and 134*a*. These three backup copies comprise the entirety of backup data set 122*a*. The result of steps 206-226 is that main controller 100 receives, and stores within memory 104, a backup copy 122*a* of the data set 122 stored on battery charger circuit board 56.

Steps 206-226 are repeated by main controller 100 for communications with actuator control circuit board 58. These repeated steps are identified in FIG. 8 with the reference numbers 206*a* through 226*a*. At step 206*a*, main controller 100 sends a request to actuator control circuit board 58 requesting that actuator controller 112 send it a copy of its PID data subset 140. Prior to this request, main circuit board 54 does not contain the backup copy 140*a* (see FIG. 5) in its memory 104. At step 208*a*, actuator controller 112 sends the backup copy 140*a* to main circuit board 54. At step 210*a*, main controller 100 stores this backup copy 140*a* in its memory 104.

At step 214*a*, main controller 100 sends the second copy 120*b* of its main PID data set 120 to actuator control circuit board 58. After receipt of this second copy 120*b*, actuator controller 112 stores this second copy 120*b* in its local memory 116 at step 216*a*. Prior to the receipt of this second copy 120*b*, actuator control circuit board 58 does not contain the second backup copy 120*b* (see FIG. 5) in its memory 116.

At step 218*a* (FIG. 8), main controller 100 sends a request to actuator controller 112 requesting a backup copy 142*a* of the actuator control circuit board fault tracking data subset 142. Prior to the receipt of this backup copy 142*a*, main circuit board 54 does not contain a backup copy 142*a* of actuator control circuit board 58's fault tracking data subset 142. The backup copy 142*a* is sent to main controller 100 at step 220*a*.

At step 222*a* (FIG. 8), main controller 100 sends a request to actuator controller 112 requesting a backup copy 144*a* of the actuator control circuit board statistics data subset 144. Prior to the receipt of this backup copy 144*a*, main circuit board 54 does not contain a backup copy 144*a* of actuator control circuit board 58's statistics data subset 144. The backup copy 144*a* is sent to main controller 100 at step 224*a*.

At step 228 (FIG. 8), main controller 100 sends a request to actuator controller 112 requesting a backup copy 146*a* of the actuator control circuit board calibration data subset 146. Prior to the receipt of this backup copy 146*a*, main circuit board 54 does not contain a backup copy 146*a* of actuator control circuit board 58's calibration data subset 146. The backup copy 146*a* is sent to main controller 100 at step 230.

At step 226*a*, main controller 100 stores all of the backup copies of data it has received from actuator control circuit board 58 in its local memory 104. These backup copies include backup copies of data subsets 140*a*, 142*a*, 144*a* and 146*a*. These four backup copies comprise the entirety of backup data set 124*a*. The result of steps 206*a*-226*a* and 228, 230 is that main controller 100 receives, and stores within memory 104, a backup copy of the data set 124 stored on actuator control circuit board 58.

After step 230 ends, algorithm 168 terminates and is generally not executed again, unless, for example, all three circuit boards are replaced at once (or all four are replaced at once, if circuit board 86 is included). The result of the execution of algorithm 168 is that main circuit board 54 ends up with a local copy 122*a* of the data stored on battery charger circuit board 56 and a local copy 124*a* of the data stored on actuator control circuit board 58. Further, battery charger circuit board 56 ends up with a first backup copy 120*a* of the data set 120 stored on main circuit board 54 and actuator control circuit board 58 ends up with a second backup copy 120*b* of that same data 120. As was noted previously, during operation of patient support apparatus 20, the battery charger controller 106 makes updates to the data in data subsets 130, 132, and 134 stored in its local memory 110, as appropriate, and also sends those updates to main controller 100 so that main controller 100 can make the same updates to its local copies 130*a*, 132*a*, and 134*a*. Similarly, during operation of patient support apparatus, actuator controller 112, makes updates to the data in data subsets 140, 142, 144, and 146 stored in its local memory 116, as appropriate, and also sends those updates to main controller 100 so that main controller 100 can make the same updates to its local copies 140*a*, 142*a*, 144*a*, and 146*a*.

It may be noted that neither battery charger circuit board 56 nor actuator control circuit board 58 include copies of any data from main controller 100 other than the backup copies 120*a* and 120*b* of the main PID file. In other words, circuit boards 56 and 58 do not contain any backup copies of fault data, statistical data, or calibration data from main circuit board 54. This is because, in at least one embodiment, main circuit board 54 does not generate any fault data or statistical data with respect to main circuit board 54, nor does it contain any calibration data regarding main circuit board 54 or any of the components directly coupled to main circuit board 54 (e.g. height sensor 76, in-ambulance sensor 74, etc.) It will be understood, however, that this may be modified in some embodiments. Thus, in some embodiments, patient support apparatus 20 is modified so that main controller 100 generates and stores fault data, statistical data, and/or calibration data regarding main circuit board 54 and not only saves it in memory 104, but also sends a first backup copy of this data to battery charger circuit board 56 for storage in memory 110 and a second backup copy of this data to circuit board 58 for storage in memory 116. Still other modifications may be made.

Figure 9:
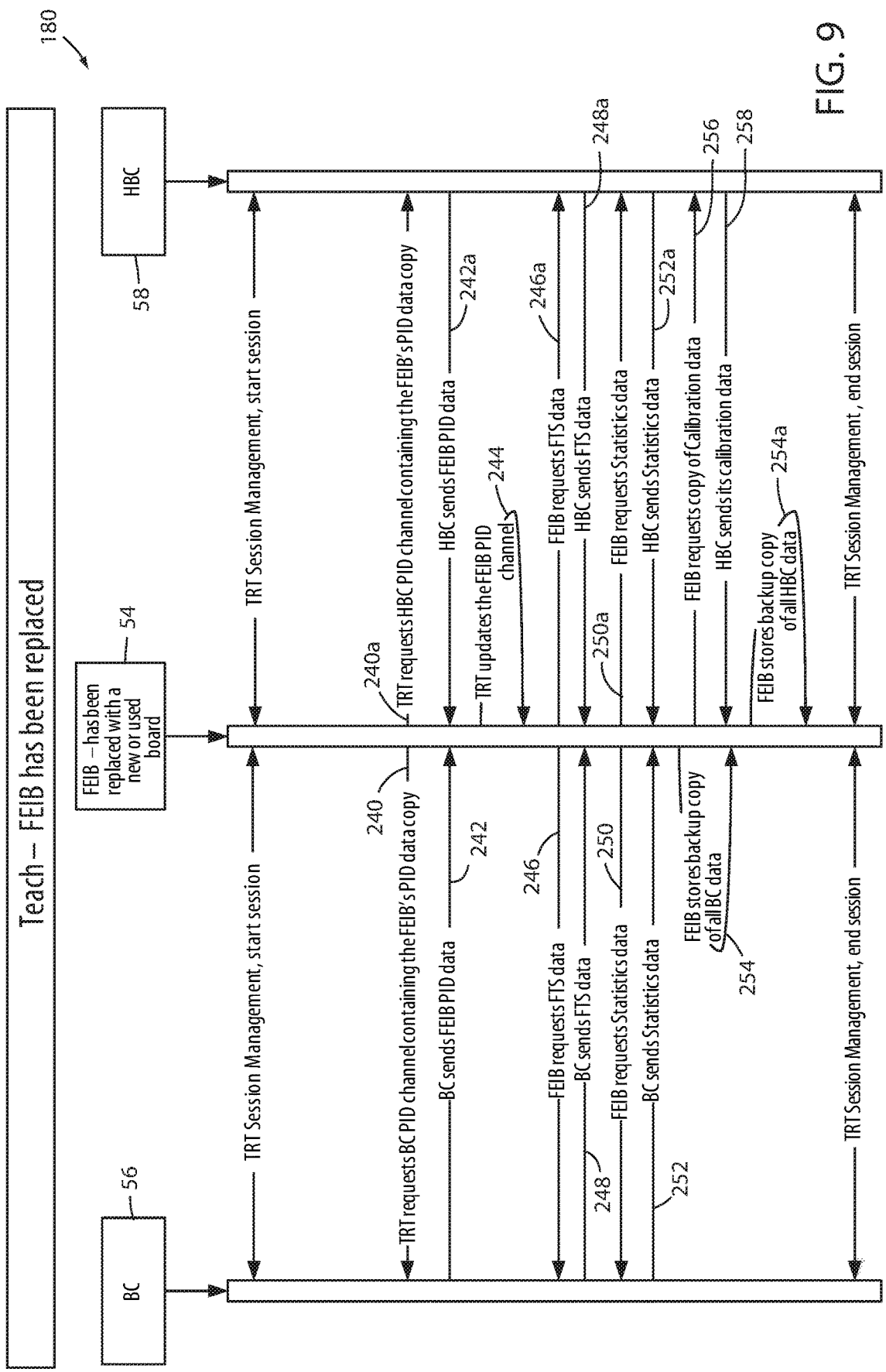
FIG. 9 is a diagram of a main circuit board replacement detection algorithm executed by the patient support apparatus of FIG. 1.

FIG. 9 illustrates one example of the main circuit board replacement algorithm 180. As was noted previously, main controller 100 (in conjunction with battery charger controller 106 and actuator controller 112) is configured to execute algorithm 180 in response to a determination at step 176 (FIG. 7) that patient support apparatus 20 contains a newly installed main circuit board 54. Main controller 100 starts algorithm 180 at a step 240 where it sends a request to battery charger circuit board 56 requesting that battery charger controller 106 send a copy of the data contained in backup data set 120*a* to main controller 100. At step 242, battery charger controller 106 complies with this request. At step 242*a*, main controller 100 sends the same request to actuator control circuit board 58 requesting that actuator controller 112 send it a copy of the data contained in backup data set 120*b*. At step 242*a*, actuator controller 112 complies with this request. At step 244, main controller 100 compares the data from backup copy 120*a* it received from battery charger circuit board 56 with the data from backup copy 120*b* it received from actuator control circuit board 58. In normal circumstances, the data from both of these backup copies 120*a* and 120*b* will match. If they do not, main controller 100 issues an error and, in some embodiments, terminates main board replacement algorithm 180. If they do match, main controller uses one of the backup sets of data 120a or 120b (doesn't matter which since they are the same) and writes that data into local memory 104 as data set 120. As a result, the newly installed main circuit board 54 gets its data set 120 populated by the data from the backup copies 120a and/or 120b maintained on circuit boards 56 and 58, thereby avoiding the need for a technician to manually transfer this data to the newly installed circuit board.

At step 246 (FIG. 9), main controller 100 sends a request to battery charger controller 106 requesting a backup copy 132a of the battery charger circuit board fault tracking data subset 132. Prior to the receipt of this backup copy 132a, main circuit board 54 does not contain a backup copy 132a of data subset 132 because it is a newly installed circuit board 54. The backup copy 132a is sent to main controller 100 at step 248.

At step 250 (FIG. 9), main controller 100 sends a request to battery charger controller 106 requesting a backup copy 134a of the battery charger circuit board statistics data subset 134. Prior to the receipt of this backup copy 134a, main circuit board 54 does not contain a backup copy 134a of data subset 134 because, as noted, it is a newly installed circuit board 54. The backup copy 134a is sent to main controller 100 at step 252.

Although not shown in FIG. 9, main controller 100 also sends a request to battery charger controller 106 requesting a backup copy 130a of the battery charger product ID data subset 130. Prior to the receipt of this backup copy 130a, main circuit board 54 does not contain a backup copy 130a of data subset 130 because, as noted, it is a newly installed circuit board 54. The backup copy 130a is sent to main controller 100 at a step not illustrated in FIG. 9.

At step 254, main controller 100 stores all of the backup copies of data it has received from battery charger circuit board 56 in its local memory 104. These backup copies include backup copies of data subsets 130a, 132a, and 134a. These three backup copies comprise the entirety of backup data set 122a. The result of the aforementioned steps is that main controller 100 receives, and stores within memory 104, a backup copy 122a of the data set 122 stored on battery charger circuit board 56.

Steps 246-254 are repeated by main controller 100 for communications with actuator control circuit board 58. These steps are identified in FIG. 9 with the reference numbers 246a through 254a. At step 246a, main controller 100 sends a request to actuator control circuit board 58 requesting that actuator controller 112 send it the data stored in backup copy 142a of the actuator control circuit board fault tracking data subset 142. Prior to the receipt of this backup copy 142a, main circuit board 54 does not contain a backup copy 142a of actuator control circuit board 58's fault tracking data subset 142. The backup copy 142a is sent to main controller 100 at step 248a.

At step 250a (FIG. 9), main controller 100 sends a request to actuator controller 112 requesting a backup copy 144a of the actuator control circuit board statistics data subset 144. Prior to the receipt of this backup copy 144a, main circuit board 54 does not contain a backup copy 144a of actuator control circuit board 58's statistics data subset 144. The backup copy 144a is sent to main controller 100 at step 248a.

At step 256 (FIG. 9), main controller 100 sends a request to actuator controller 112 requesting a backup copy 146a of the actuator control circuit board calibration data subset 146. Prior to the receipt of this backup copy 146a, main circuit board 54 does not contain a backup copy 146a of actuator control circuit board 58's calibration data subset 146. The backup copy 146a is sent to main controller 100 at step 258.

Further, although not shown in FIG. 9, main controller 100 also sends a request to actuator controller 112 requesting a backup copy 140a of the actuator product ID data subset 140. Prior to the receipt of this backup copy 140a, main circuit board 54 does not contain a backup copy 140a of data subset 144 because, as noted, it is a newly installed circuit board 54. The backup copy 140a is sent to main controller 100 at a step not illustrated in FIG. 9.

At step 254a (FIG. 9), main controller 100 stores all of the backup copies of data it has received from actuator control circuit board 58 in its local memory 104. These backup copies include backup copies of data subsets 140a, 142a, 144a and 146a. These four backup copies comprise the entirety of backup data set 124a. The result of the aforementioned steps is that main controller 100 receives, and stores within memory 104, a backup copy 124a of the data set 124 stored on actuator control circuit board 58.

After step 254a is completed by main controller 100, algorithm 168 terminates and is generally not executed again until main circuit board 54 is once again replaced. The result of the execution of algorithm 180 is that the newly installed main circuit board 54 ends up with a local copy 122a of the data stored on battery charger circuit board 56 and a local copy 124a of the data stored on actuator control circuit board 58. The historical data contained within data subsets 130, 132, 134, 140, 142, 144, and 146, which was backed up on the previously installed main circuit board 54, is therefore—after execution of algorithm 180—backed up on the newly installed main circuit board 54 in its memory 104.

Figure 10:
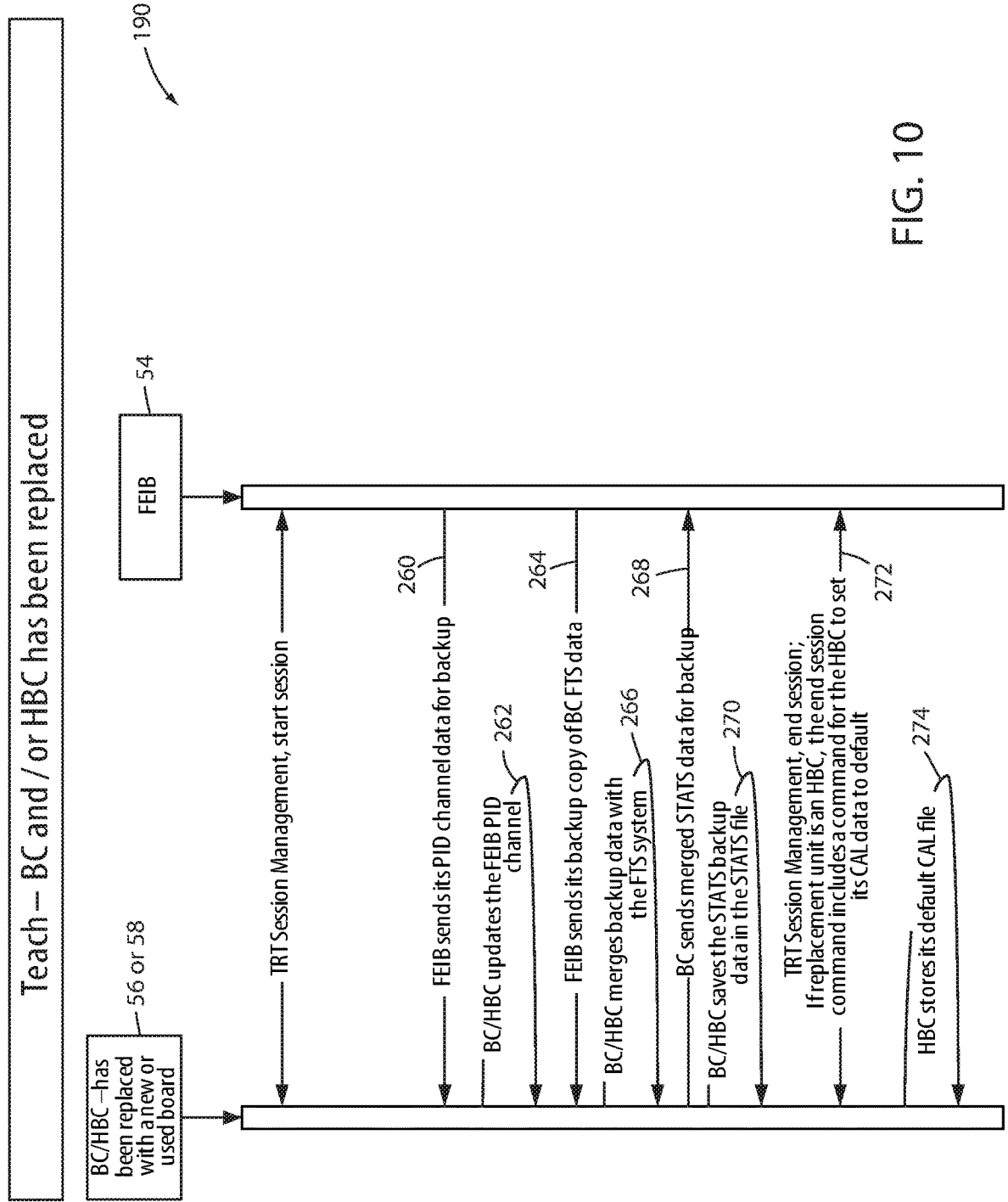
FIG. 10 is a diagram of a peripheral circuit board replacement algorithm executed by the patient support apparatus of FIG. 1.

FIG. 10 illustrates one example of the replacement board algorithm 190. As was noted previously, main controller 100 (in conjunction with battery charger controller 106 or actuator controller 112) is configured to execute algorithm 190 in response to a determination at step 178 (FIG. 7) that patient support apparatus 20 contains either a newly installed battery charger circuit board 56, or a newly installed actuator control circuit board 58. Main controller 100 starts algorithm 190 at a step 260 where it sends to whichever circuit board 56 or 58 (or 86, if present and newly replaced) that has been newly installed a copy (120a or 120b) of data set 120. The receiving board stores the backup copy 120a or 120b in its local memory (110 or 116) at step 262. At step 264, main controller 100 sends to the newly installed circuit board (56, 58, or 86) a copy of that board's backup fault tracking data, e.g. a copy of data subset 132a from memory 104 to circuit board 56 or a copy of data subset 142a from memory 104 to board 58. (If board 86 is present, main controller 100 maintains a fault tracking data subset for board 86 similar to the fault tracking data subsets it maintains for circuit board 56 and 58). At step 266, the controller in the newly installed board merges the received copy of its fault tracking data with whatever fault tracking data it may already have placed in its local fault tracking file (contained with either data subset 132 or 142).

At step 268 (FIG. 10), controller 100 sends to the newly installed circuit board 56, 58, or 86, a copy of that board's backup statistical data, e.g. a copy of data subset 134a from memory 104 to circuit board 56 or a copy of data subset 144a from memory 104 to board 58. (If board 86 is present, main controller 100 maintains a statistics data subset for board 86 similar to the statistics data subsets it maintains for circuit board 56 and 58). At step 270, the controller in the newly installed board merges the received copy of its statistics data with whatever statistical data it may already have placed in its local fault tracking file (contained with either data subset 134 or 144).

At step 272, algorithm 190 ends if the newly installed circuit board is the battery charger circuit board 56. If the newly installed circuit board is the actuator control circuit board, main controller 100 sends a message at step 272 to actuator controller 112 instructing it to set its calibration data subset 146 to a set of default calibration data. At step 274, actuator controller 112 stores this default calibration data subset 146 in its local memory 116. At some subsequent point in time, this calibration data may be updated with fresh calibration data that is specific to the newly installed actuator control circuit board 58. However, in some embodiments, if the calibration data from one actuator control circuit board 58 to another actuator control circuit board 58 remains the same, then step 272 may be modified such that main controller 100 simply sends a copy of its backup calibration data subset 146a to actuator control circuit board 58 (which stores it in memory 116) and there is no use of any default data. In still other modified embodiments, main controller 100 may be configured to supply some calibration data to a newly installed actuator control circuit board 58 from its backup copy 146a and the newly installed actuator control circuit board 58 may use some default calibration data until it is calibrated. Still other modifications are possible. After step 274, algorithm 190 ends.

Figure 11:
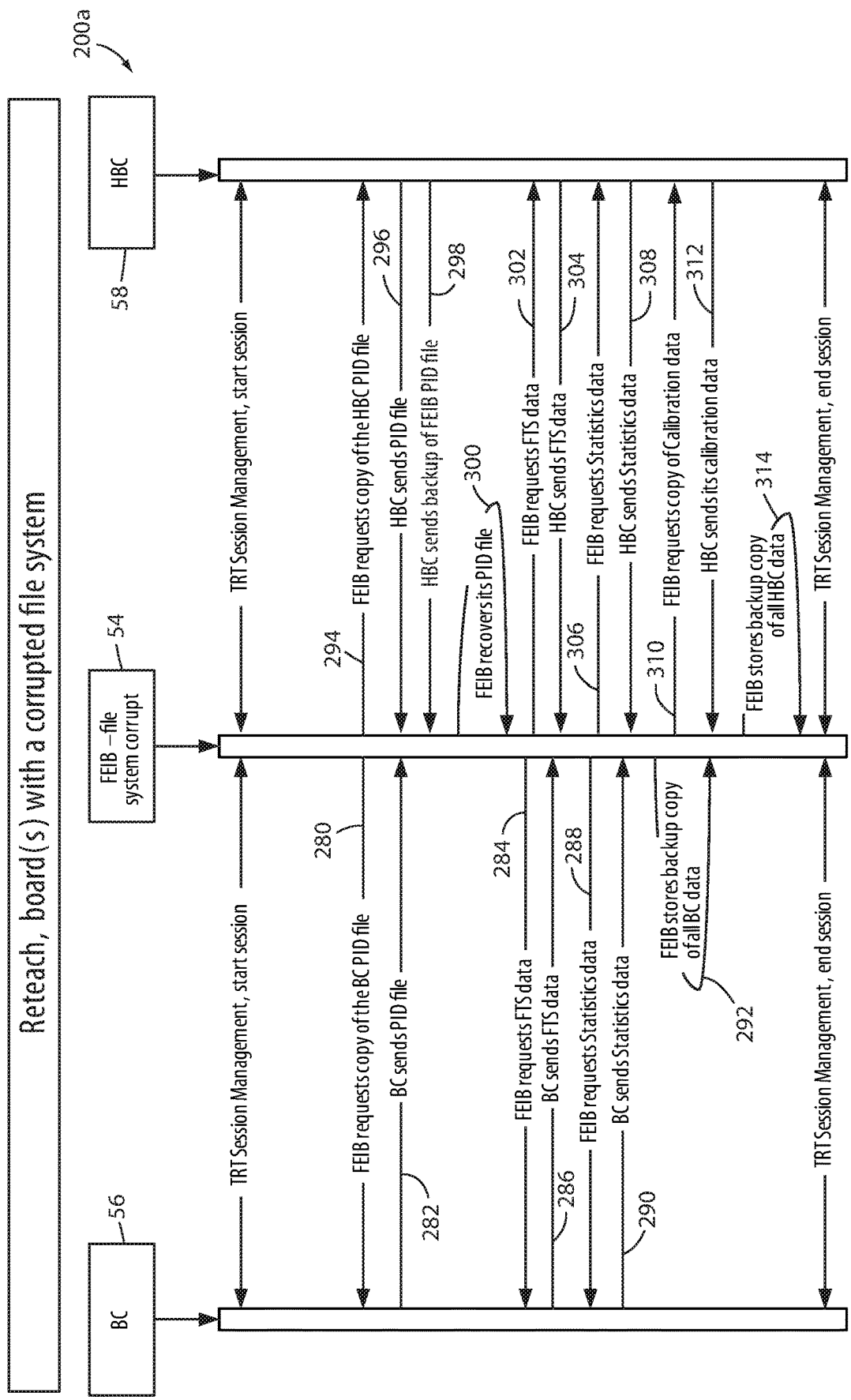
FIG. 11 is a diagram of a corrupt file system replacement algorithm executed by the patient support apparatus of FIG. 1 when a corrupt file system is detected on the main circuit board.
Figure 12:
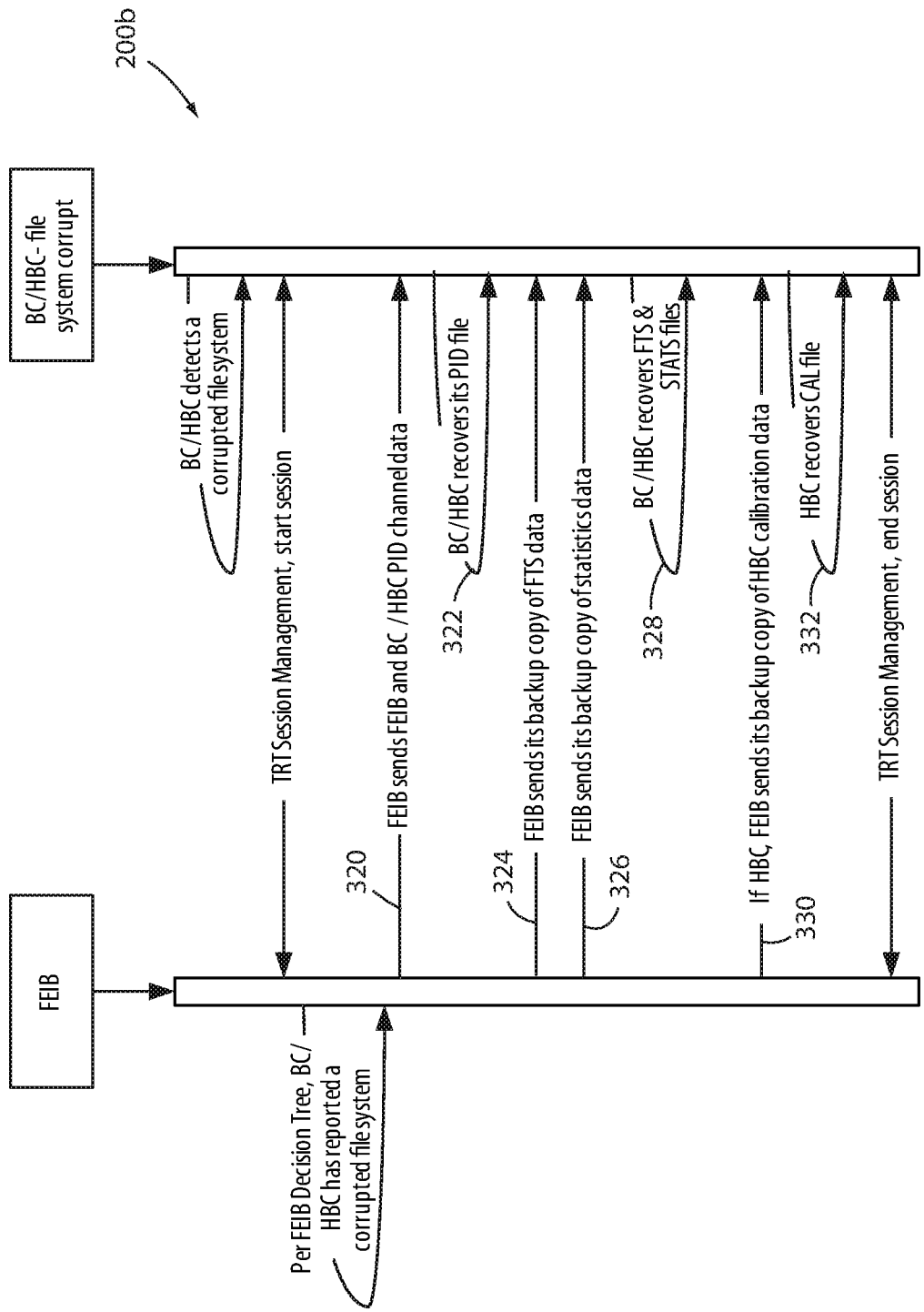
FIG. 12 is a diagram of a corrupt file system replacement algorithm executed by the patient support apparatus of FIG. 1 when a corrupt file system is detected on one of the peripheral circuit boards.

FIG. 11 illustrates one example of a corrupt file system replacement algorithm 200a. As was noted previously, main controller 100 (in conjunction with battery charger controller 106 or actuator controller 112) is configured to execute either algorithm 200a or 200b in response to a determination at step 172 (FIG. 7) that patient support apparatus 20 contains a circuit board with a corrupt file system. If the corrupt file system is contained onboard main circuit board 54, main controller 100 executes algorithm 200a. If the corrupt file system is contained onboard battery charger circuit board 56 or actuator control circuit board 58 (or communication board 86, if present), then main controller 100 executes algorithm 200b (FIG. 12).

Turning first to corrupt file system replacement algorithm 200a (FIG. 11), main controller 100 detects that it has a corrupt file system within memory 104 during step 172 of algorithm 160. After making this detection, main controller 100 commences execution of algorithm 200a at step 280. Main controller 100 follows up step 280 with steps 284 and 288. Steps 280, 284, and 288 of algorithm 200a are the same as steps 206, 218, and 222 of algorithm 168 (FIG. 8). Battery charger controller 106 also executes steps 282, 286, and 290 as part of algorithm 200a, and these steps are the same as steps 208, 220, and 224 of algorithm 168. Consequently, none of these steps needs to be re-described herein. The result of the execution of these steps 280 through 290 is that main circuit board 54 is supplied with a non-corrupt copy of the battery charger boards' data subsets 130, 132, and 134. Main controller 100 stores this non-corrupt data in memory 104 as backup copies 130a, 132a, and 134a at step 292.

Main controller 100 also executes steps 294, 302, and 306, which are the same as steps 206a, 218a, and 222a of algorithm 168 (FIG. 8). Further, actuator controller 112 executes steps 296, 304, and 308 as part of algorithm 200a, and these steps are the same as steps 208a, 220a, and 224a of algorithm 168. Consequently, none of these steps needs to be re-described herein. The result of the execution of these steps is that main circuit board 54 is supplied with a non-corrupt copy of the actuator control circuit board's data subsets 140, 142, and 144. Main controller 100 further sends a request at step 310 to actuator controller 112 for a copy of its calibration data subset 146. At step 312, actuator controller 112 responds to this request and sends a copy 146a of its calibration data subset to main controller 100. At step 314, main controller 100 stores all of the data it has received from actuator control circuit board (e.g. backup copy 124a) in memory 104. Algorithm 200a then ends.

The result of algorithm 200a is that all of the data within the corrupt file system onboard main circuit board 54 is replaced by the data sets 122 and 124 stored on circuit boards 56 and 58. Although not illustrated in FIG. 11, algorithm 200a may further be modified to send either or both of backup copies 120a and/or 120b to main circuit board 54 so that main controller 100 may re-save this Product ID data to memory 104 (in case data set 120 has been detected as being corrupt). Still other modifications can be made.

Turning now to corrupt file system replacement algorithm 200b (FIG. 12), main controller 100 detects that one or both of battery charger circuit board 56 or actuator control circuit board 58 has a corrupt file system within its memory 110 and/or 116 during step 172 of algorithm 160. After making this detection, main controller 100 commences execution of algorithm 200b at step 320. At step 320, main controller 100 sends one of backup data subsets 130a or 140a to whichever circuit board 56 or 58 has the corrupt file system (if both do, main controller 100 repeats algorithm 200b sequentially, once for one of the boards and the second time for the other one of the boards). The recipient board receives the data at step 322 and records it in its local memory 110 or 116. At step 324, main controller 100 sends one of the backup data subsets 132a or 142a to whichever circuit board 56 or 58 has the corrupt file system. At step 326, main controller 100 sends one of the backup data subsets 134a or 144a to whichever circuit board 56 or 58 has the corrupt file system. At step 328, the recipient board 56 or 58 receives the data from steps 324 and 326 and records that data in its local memory 110 or 116. If the recipient board with the corrupted file system is the actuator control circuit board 58, then main controller 100 also completes step 330, during which it sends a copy of data subset 146a to actuator control circuit board 58, which then saves that data in its local memory 116 at step 332. This data saving overwrites the corrupted data in the corrupted file system. After step 332, algorithm 200b ends.

The result of algorithm 200b is that main controller 100 provides whichever circuit board 56 or 58 (or 86, if present) has the corrupt file system with a fresh and non-corrupt copy of the backup data that is stored in memory 104 of main circuit board 54. The recipient board uses this non-corrupt copy of the backup data to overwrite the corrupted data. The data that was contained in the corrupted file system is therefore restored to that board.

Figure 13:
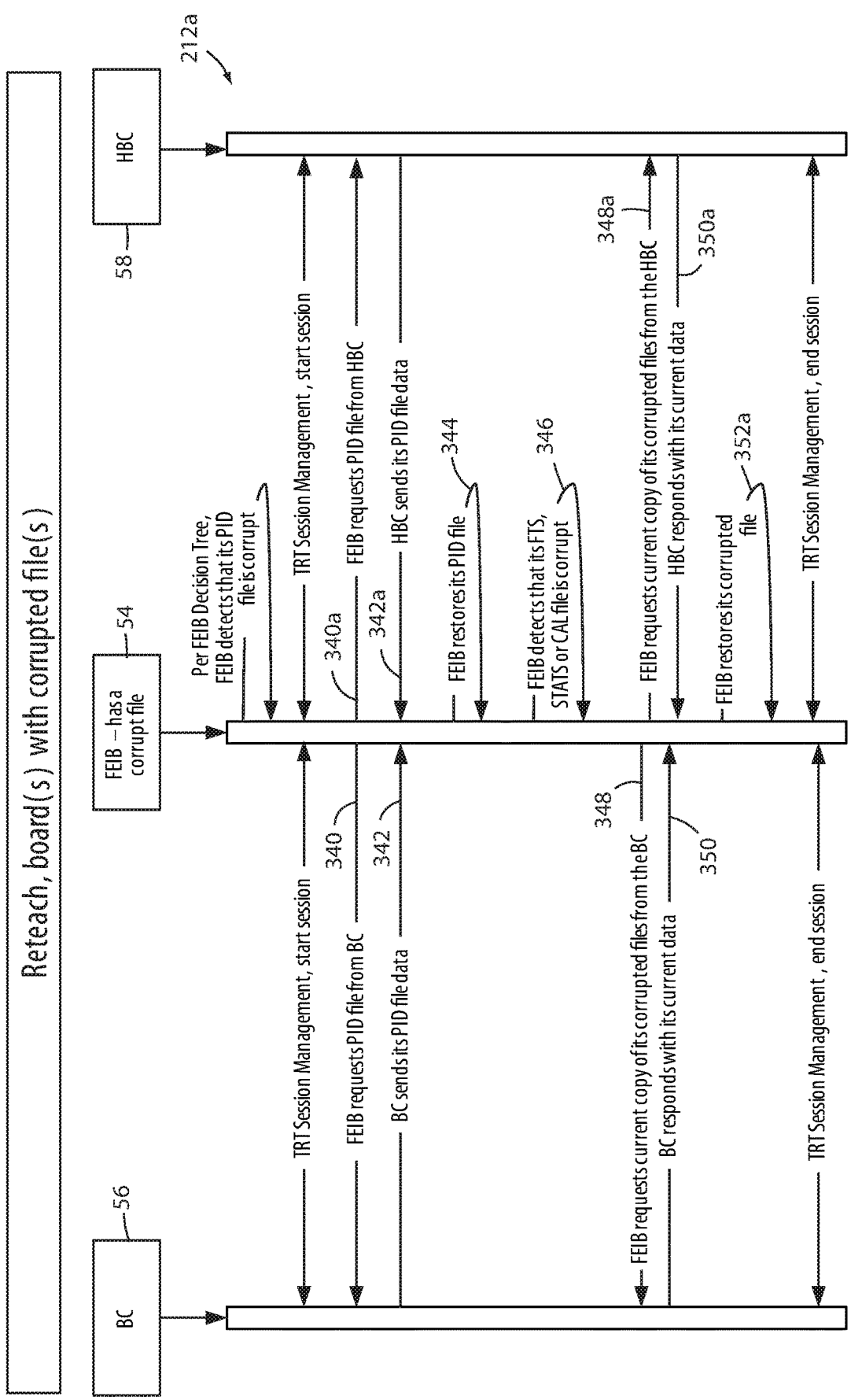
FIG. 13 is a diagram of a corrupt file algorithm followed by the patient support apparatus of FIG. 1 when an individually corrupted file is detected on the main circuit board.
Figure 14:
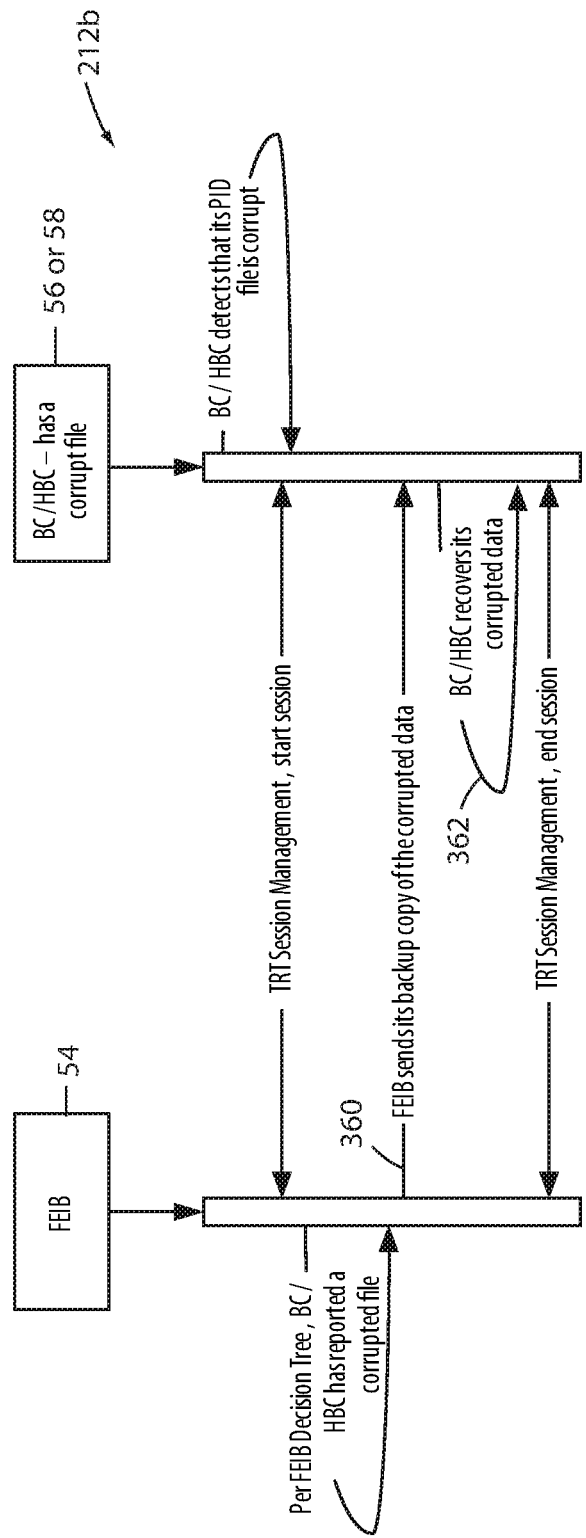
FIG. 14 is a diagram of a corrupt file algorithm followed by the patient support apparatus of FIG. 1 when an individually corrupted file is detected on one of the peripheral circuit boards.

FIG. 13 illustrates one example of a corrupt file replacement algorithm 212a. As was noted previously, main controller 100 (in conjunction with battery charger controller 106 or actuator controller 112) is configured to execute either algorithm 212a or 212b in response to a determination at step 188 (FIG. 7) that patient support apparatus 20 contains a circuit board with a corrupt file. If the corrupt file is contained onboard main circuit board 54, main controller 100 executes algorithm 212a. If the corrupt file is contained onboard battery charger circuit board 56 or actuator control circuit board 58 (or communication board 86, if present), then main controller 100 executes algorithm 212b (FIG. 14).

Turning first to corrupt file replacement algorithm 212a (FIG. 13), main controller 100 detects that it has a corrupt file within memory 104 during step 188 of algorithm 160

(FIG. 7). After detecting the corrupt file within memory 104, main controller 100 commences execution of algorithm 212a at step 340 where it sends a request to battery charger circuit board 56 requesting the data stored in the first backup copy 120a of the main circuit board's PID data set. Main controller 100 may also send a similar request at step 340a to actuator control circuit board 58 requesting the data stored in the second backup copy 120b of the main circuit board's PID data set. At steps 342 and 342a, the battery charger circuit board 56 and the actuator control circuit board 58, respectively, respond with the requested data. At step 344, main controller restores it Product ID data set 120 using the data from one or both of the backup copies 120a and/or 120b received at steps 342 and/or 342a. In some embodiments, main controller 100 may omit steps 340a and 342a and simply use the backup data 120a from battery charger circuit board 56, or it may alternatively omit steps 340 and 342 and simply use the backup data 120b from actuator control circuit board 58.

At step 346, main controller 100 determines if any of the files contained within its backup data sets 122a and/or 124a is corrupt. If so, main controller proceeds to steps 348 and/or 348a. If not, algorithm 212a ends. At step 348, main controller 100 sends a request to battery charger circuit board 56 requesting a copy of one or more of the data subsets 130, 132, and/or 134, depending upon which of these data subsets contains a corrupt file. Battery charger circuit board 56 responds with the requested data at step 350, and controller 100 uses the requested data to overwrite the corrupted file.

At step 348a (FIG. 13), main controller 100 sends a request to actuator control circuit board 58 requesting a copy of one or more of the data subsets 140, 142, 144, and/or 146, depending upon which of these data subsets contains a corrupt file. Actuator control circuit board 58 responds with the requested data at step 350a, and controller 100 uses the requested data to overwrite the corrupted file.

If the corrupt file(s) on board main circuit board 54 do not pertain to any data that is backed up on battery charger circuit board 56, steps 348 and 350 may, of course, be omitted from algorithm 212a. Similarly, if the corrupt file(s) on board main circuit board 54 do not pertain to any data that is backed up on actuator control circuit board 58, steps 348a and 350a may also be omitted.

The result of algorithm 212a is that any files stored onboard main circuit board 54 that were previously corrupt are replaced using one or more of their backup copies stored onboard one of the other circuit boards (e.g. 56, 58, and/or 86).

FIG. 14 illustrates one example of a corrupt file replacement algorithm 212b that is executed when a corrupt file is detected onboard battery charger circuit board 56 and/or actuator control circuit board 58 (or communication board 86, if present). Main controller 100 begins executing algorithm 212b when it determines at step 188 of algorithm 160 that either the battery charger circuit board 56 or the actuator control circuit board 58 contains a corrupt file. Main controller 100 begins algorithm 212b at a step 360 where it sends a non-corrupted set of backup data to whichever board(s) (56, 58, and/or 86) reported having a corrupt file. Thus, if battery charger circuit board 56 reports having a corrupt file, main control board sends all or a portion of its backup set of data 122a to battery charger circuit board 56. If actuator control circuit board 58 reports having a corrupt file, main controller 100 sends all or a portion of its backup set of data 124a to actuator control circuit board 58. For both situations, the local controller (either battery charger controller 106 or actuator controller 112) stores the received non-corrupted data at step 362. Algorithm 212b then ends, and the result of algorithm 212b is that any files stored on circuit boards 56, 58, and/or 86 that were previously corrupt are replaced using the backup copy stored on main circuit board 54.

Although not shown in FIG. 5, control system 52 may be modified to include a wireless communication circuit board 86, as alluded to above. When included, the circuit board 86 stores its own set of data (e.g. Product ID file, fault tracking, statistics, etc.) on its own local memory, and may also send a backup copy of this data to the main circuit board 54. The aforementioned algorithms are then utilized in the same manner discussed above with respect to circuit boards 54, 56, and 58 to automatically detect if circuit board 86 is a recent replacement for a previously installed circuit board 86, and/or if it has any corrupt files. The detection of whether circuit board 86 is a recently installed replacement for a previous circuit board 86 is accomplished in generally the same manner discussed above. That is, main controller 100 concludes that circuit board 86 is a newly installed replacement if the Product ID file stored onboard circuit board 86 doesn't match the backup copy stored onboard main circuit board 54 and main circuit board's Product ID file (stored in memory 104) matches the backup copies 120a and/or 120b stored onboard circuit boards 56 and/or 58.

It should also be noted that the aforementioned algorithms for automatically detecting a newly installed circuit board are primarily designed to detect new circuit boards when circuit boards are replaced one at a time (e.g. only one circuit board is replaced between each iteration of algorithm 160). In some embodiments, the algorithms may be modified and/or supplemented to detect when multiple circuit boards are replaced at once. For example, in some embodiments, two boards may be designated as primary circuit boards such that any number of boards beyond those two may be replaced at once. If the PID data from those two boards matches but differs from the other board(s), then the system concludes that any boards not having the same PID data as the two primary boards are replacement boards. If the PID data from those two boards matches, as well as the PID data from the other board(s), then no boards have been replaced. In this system, the primary boards are not able to be replaced at one time, but any number of non-primary boards may be replaced at one time. In still other embodiments, one or more electronic components may be integrated into patient support apparatus 20 that are not coupled to a removable circuit board. In such embodiments, these components may take a snap shot of the product IDs of each of the boards and store it in a local memory. Any product IDs that are different from what is stored in the components during the next power cycle are then considered to be replacements. Still other manners for automatically determining if multiple boards have been replaced at once are possible.

After the various controllers of circuit boards 54, 56, and 58 (and 86, if included) have performed the algorithms illustrated in FIGS. 6-14, these controllers switch to carrying out their normal functions during the operation of patient support apparatus 20. As was noted previously, this operation may involve one or more of the controllers updating the contents of the data stored in data sets 120, 122 and/or 124. Such alterations are communicated to the other boards so that the backup copies illustrated in FIG. 5 are updated. In some embodiments, the communication of these backup sets of data occurs in real time, while in other embodiments the communication of these backup sets of data may be deferred until one or more triggering events occurs. In either situation, the circuit boards of control system 52 contain backup copies of the data contained on the other circuit boards, and this allows the circuit boards to be replaced with new circuit boards and automatically populated with the historical data that was previously generated by the previously installed circuit board(s).

It will be further understood that, although patient support apparatus 20 has been illustrated herein as being a cot for use in emergency vehicles, patient support apparatus 20 may take on other forms. For example, the algorithms discussed herein may be applied to a bed of the type disclosed in commonly assigned U.S. patent application Ser. No. 62/823, 324 filed Mar. 25, 2019, by inventors Zane Shami et al. and entitled PATIENT CARE SYSTEM WITH POWER MANAGEMENT, the complete disclosure of which is incorporated herein by reference. The beds disclosed in this '324 application may include the plurality of circuit boards illustrated in FIG. 2 of that patent application, and when the teachings of the present disclosure are applied to these circuit boards, the controllers of each of the circuit boards (or a subset of them) monitor and store backup copies of each other's data so that the circuit boards may be replaced without losing historical data, and/or corrupted files may be replaced automatically using data copies that have been backed up on one or more of the other circuit boards. The teachings of the present disclosure may also be applied to any other type of bed or other patient support that includes multiple, replaceable circuit boards.

In still other embodiments, the teachings of the present disclosure may be applied to thermal control systems having multiple, replaceable circuit boards. As one example, the teachings of the present disclosure may be applied to thermal controllers of the type disclosed in commonly assigned U.S. patent publication 2014/0343639 filed May 20, 2014, by inventors Christopher John Hopper et al. and entitled THERMAL CONTROL SYSTEM, the complete disclosure of which is incorporated herein by reference. When the teachings of the present disclosure are applied to thermal controllers of this type, the microcontrollers A, B, C, and/or D shown in FIG. 21 of this publication may be integrated into multiple circuit boards that back up each others data in the manners disclosed herein. The teachings of the present disclosure may also be applied to still other types of thermal control systems, as well as to still other types of medical devices.

In some embodiments, the data that is stored and backed up by one or more of the circuit boards 54, 56, and/or 58 (and/or 86) is sent off of patient support apparatus 20 to a cloud-based equipment management system. As noted previously, one suitable cloud-based equipment management system is disclosed in greater detail in commonly assigned PCT patent publication PCT/US2017/041681 filed Jul. 12, 2017, by inventors David Becker et al. and entitled EQUIPMENT MANAGEMENT SYSTEM, the complete disclosure of which is incorporated herein by reference. By incorporating the teachings of the present disclosure into such a cloud-based equipment management system, data that might otherwise have been lost to the cloud-based equipment management system (e.g. data lost when a circuit board was replaced prior to that circuit board sending its data to the cloud-based equipment management system) is preserved so that the equipment management system is able to retain more accurate information about the medical devices it is monitoring.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a frame;
a patient support surface supported on the frame;
a lift adapted to raise and lower the patient support surface;
a first circuit board supported by the frame and including a first controller and a first memory, the first controller adapted to store a first set of data in the first memory and to perform a first one of the following functions: (a) charge a battery, (b) control the lift; or (c) receive a sensor input;
a second circuit board supported by the frame and including a second controller and a second memory, the second controller adapted to store a second set of data in the second memory and to perform a second one of the functions (a), (b), or (c);
a third circuit board supported by the frame and including a third controller and a third memory, the third controller adapted to store a third set of data in the third memory and to perform a third one of the functions (a), (b), or (c); and
wherein the first controller is adapted to send a backup copy of the first set of data to the third circuit board, the second controller is adapted to send a backup copy of the second set of data to the third circuit board, and the third controller is adapted to store the backup copy of the first set of data and the backup copy of the second set of data in the third memory.

2. The patient support apparatus of claim 1 wherein the third controller is further adapted to send a first backup copy of the third set of data to the first circuit board and a second backup copy of the third set of data to the second circuit board, and wherein the first controller is adapted to store the first backup copy of the third set of data in the first memory and the second controller is adapted to store the second backup copy of the third set of data in the second memory.

3. The patient support apparatus of claim 1 wherein the first set of data includes a first identifier for the first circuit board and the second set of data includes a second identifier for the second circuit board.

4. The patient support apparatus of claim 3 wherein the third set of data includes a third identifier for the third circuit board, and the first controller is adapted to store a first backup copy of the third identifier in the first memory and the second controller is adapted to store a second backup copy of the third identifier in the second memory.

5. The patient support apparatus of claim 4 wherein the first controller, in response to a first triggering condition, is adapted to resend back to the third circuit board the first backup copy of the third identifier stored in the first memory, and the third controller is adapted to compare the resent first backup copy of the third identifier to a third identifier stored in the third memory.

6. The patient support apparatus of claim 5 wherein the second controller, in response to a second triggering condition, is adapted to resend back to the third circuit board the second backup copy of the third identifier stored in the second memory, and the third controller is adapted to compare the resent second backup copy of the third identifier to the third identifier stored in the third memory.

7. The patient support apparatus of claim 6 wherein, if the resent first backup copy of the third identifier matches the third identifier stored in the third memory but the resent second backup copy of the third identifier does not match the third identifier stored in the third memory, the third controller is further adapted to conclude that the second circuit board is a replacement of a previously installed second circuit board.

8. The patient support apparatus of claim 7 wherein the third controller is further adapted, after determining that the second circuit board is a replacement, to resend back to the second circuit board the second set of data stored in the third memory, and the second controller is further adapted to replace the second set of data stored in the second memory with the resent second set of data received from the third controller.

9. The patient support apparatus of claim 8 further comprising a transceiver adapted to communicate with an off-board server, the transceiver further adapted to transmit at least a portion of the resent second set of data received from the third controller to the off-board server after the second circuit board has been replaced.

10. The patient support apparatus of claim 1 wherein the first circuit board is coupled to a motor adapted to drive the lift, and the first set of data includes usage data regarding the motor.

11. The patient support apparatus of claim 1 wherein the first controller is adapted to detect if the first set of data stored in the first memory includes corrupt data and, if so, to replace the corrupt data with at least a portion of the backup copy of the first set of data stored in the third memory and received back from the third circuit board.

12. A patient support apparatus comprising:
a frame;
a patient support surface supported on the frame;
a lift adapted to raise and lower the patient support surface;
a first circuit board including a first controller and a first memory, the first controller adapted to store a first set of data in the first memory;
a second circuit board including a second controller and a second memory, the second controller adapted to store a second set of data in the second memory;
a third circuit board including a third controller and a third memory, the third controller adapted to store a third set of data in the third memory; and
wherein the first controller is adapted to send a backup copy of the first set of data to the third circuit board;
the second controller is adapted to send a backup copy of the second set of data to the third circuit board;
the third controller is adapted to store the backup copy of the first set of data and the backup copy of the second set of data in the third memory;
the first set of data includes a first identifier for the first circuit board;
the second set of data includes a second identifier for the second circuit board;
the third set of data includes a third identifier for the third circuit board;
the first controller is adapted to store a first backup copy of the third identifier in the first memory;
the second controller is adapted to store a second backup copy of the third identifier in the second memory;
the first controller, in response to a first triggering condition, is adapted to resend back to the third circuit board the first backup copy of the third identifier stored in the first memory;
the third controller is adapted to compare the resent first backup copy of the third identifier to a third identifier stored in the third memory;
the second controller, in response to a second triggering condition, is adapted to resend back to the third circuit board the second backup copy of the third identifier stored in the second memory,
the third controller is adapted to compare the resent second backup copy of the third identifier to the third identifier stored in the third memory; and if neither the resent first backup copy of the third identifier nor the resent second backup copy of the third identifier match the third identifier stored in the third memory, the third controller is further adapted to conclude that the third circuit board is a replacement of a previously installed third circuit board.

13. The patient support apparatus of claim 12 wherein the third controller is further adapted, after determining that the third circuit board is a replacement, to replace the third identifier stored in the third memory with at least one of the resent first backup copy of the third identifier from the first memory or the resent second backup copy of the third identifier from the second memory.

14. The patient support apparatus of claim 12 wherein the third identifier is a checksum value of an identification file stored in the third memory, and the identification file contains at least one unique string of characters uniquely identifying the third circuit board.

15. A patient support apparatus comprising:
a frame;
a patient support surface supported on the frame;
a lift adapted to raise and lower the patient support surface;
a first circuit board including a first controller and a first memory, the first controller adapted to store a first set of data in the first memory;
a second circuit board including a second controller and a second memory, the second controller adapted to store a second set of data in the second memory;
a third circuit board including a third controller and a third memory, the third controller adapted to store a third set of data in the third memory; and
wherein the third controller is adapted to automatically store a backup copy of the first set of data in the third memory, to determine if the first circuit board is a replacement of a previously installed first circuit board, and if so, to forward the backup copy of the first set of data to the first circuit board.

16. The patient support apparatus of claim 15 wherein the first controller is further adapted to automatically store a backup copy of the third set of data in the first memory, and the third controller is further adapted to automatically determine if the third circuit board is a replacement of a previously installed third circuit board and, if so, to retrieve a backup copy of the third set of data from the first memory and to replace the third set of data stored in the third memory with the backup copy of the third set of data from the first memory.

17. The patient support apparatus of claim 16 wherein, in response to the third controller determining that the third circuit board is a replacement of a previously installed third circuit board, the third controller is further adapted to retrieve another backup copy of the first set of data from the first circuit board, to retrieve another backup copy of the second set of data from the second circuit board, and to store the another retrieved copies of the first and second sets of data in the third memory.

18. The patient support apparatus of claim 16 wherein the third controller is adapted to automatically determine if the third circuit board is a replacement of a previously installed third circuit board by comparing an identifier associated with the third circuit board and stored in the third memory with a first backup identifier stored in the first memory and a second backup identifier stored in the second memory, and wherein if the identifier is different from both the first backup identifier and the second backup identifier, the third controller determines that the third circuit board is a replacement of a previously installed third circuit board.

19. The patient support apparatus of claim 15 wherein the first controller is further adapted to determine if any of the first set of data stored in the first memory is corrupt and, if so, to retrieve from the third circuit board the backup copy of the first set of data stored in the third memory, and to overwrite the corrupt data with the retrieved backup copy of the first set of data.

20. The patient support apparatus of claim 15 wherein the first set of data includes an identifier of the first circuit board and the third controller is adapted to determine if the first circuit board is a replacement of a previously installed first circuit board by comparing the identifier of the first circuit board with a backup copy of an identifier stored in the third memory.

* * * * *